United States Patent
Bawa et al.

(10) Patent No.: US 8,630,876 B1
(45) Date of Patent: *Jan. 14, 2014

(54) HEALTH SERVICE DELIVERY TABLES SYSTEM AND METHOD

(71) Applicant: Humana Inc., Louisville, KY (US)

(72) Inventors: Dilpreet Bawa, Louisville, KY (US);
Leah Brucchieri, Louisville, KY (US);
John Morgan, Pewee Valley, KY (US);
Shyam Rebello, Louisville, KY (US);
Sarah Rogers, Louisville, KY (US)

(73) Assignee: Humana Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,700

(22) Filed: Jan. 8, 2013

Related U.S. Application Data

(63) Continuation of application No. 12/956,848, filed on Nov. 30, 2010, now Pat. No. 8,352,286.

(51) Int. Cl.
*A61B 5/00* (2006.01)
(52) U.S. Cl.
USPC .................................................. 705/3; 705/2
(58) Field of Classification Search
USPC .......................................................... 705/3, 2
See application file for complete search history.

(56) References Cited

U.S. PATENT DOCUMENTS

| | | | | |
|---|---|---|---|---|
| 6,151,581 | A | * | 11/2000 | Kraftson et al. ............... 705/3 |
| 6,532,459 | B1 | * | 3/2003 | Berson ........................... 1/1 |
| 2009/0043612 | A1 | * | 2/2009 | Szela et al. ..................... 705/3 |

OTHER PUBLICATIONS

Google search result for parent U.S. Appl. No. 12/956,848, filed Sep. 25, 2013.*
Google patents search result for parent U.S. Appl. No. 12/956,848, filed Sep. 25, 2013.*
ProQuest search result for parent U.S. Appl. No. 12/956,848, filed Sep. 25, 2013.*

* cited by examiner

*Primary Examiner* — Dilek B Cobanoglu
(74) *Attorney, Agent, or Firm* — Stanley Law Group LLP

(57) ABSTRACT

A computerized system and method for generating CMS-compliant health services delivery (HSD) tables. A database stores health care service provider data. A remote computer user interacts with a server that provides access to the health care service provider data. A user can view health care service provider data that meets selected search parameters. The data is displayed in an interactive worksheet. The user may further cause amendments to be made to the data stored in the database. The user may issue a request to generate an HSD table in "final file format" which conforms to CMS requirements. The server checks for errors in the file and notifies the user of errors that are identified. The server optionally checks for adequacy of the network associated with a plurality of health care service providers. The user may approve the final files for filing with CMS.

20 Claims, 37 Drawing Sheets

County Coverage Update Form

The County Coverage Update sheet is intended to capture input from the market where they might have locally contracted provider that covers counties BESIDES the county it is physically located in - similar to the way that Ancillary's Home Health and DME providers tend to do.

When the sheet is initially spawned, there will only be one line for each provider the user has marked as needing county coverage:

| PidKey | Facility Name | Office Master Key | Physical Location Address | Physical Location City | Physical Location State | Physical Location Zip Code | Physical Location County | Coverage State | Coverage County |
|---|---|---|---|---|---|---|---|---|---|
| 12345 | Sample DME | 43123 | 555 Example St. | Sampletown | KY | 40064 | Nelson | | |
| 65381 | Home Health of Jefferson County | 55221 | 123 Another St. | Louisville | KY | 40206 | Jefferson | | |

700

Continued on next slide

FIG. 13

County Coverage Update Form

If a provider covers only one county in addition to the county it is physically located in, the user would simply add the information in the "Coverage State" and "Coverage County" field. If a provider covers multiple counties in addition to the county it is physically located in, the user will need to provide one row per county covered. For example:

| PidKey | Facility Name | Office Master Key | Physical Location Address | Physical Location City | Physical Location State | Physical Location Zip Code | Physical Location County | Coverage State | Coverage County |
|---|---|---|---|---|---|---|---|---|---|
| 12345 | Sample DME | 43123 | 555 Example St. | Sampletown | KY | 40004 | Nelson | KY | Marion |
| 12345 | Sample DME | 43123 | 555 Example St. | Sampletown | KY | 40004 | Nelson | KY | Spencer |
| 12345 | Sample DME | 43123 | 555 Example St. | Sampletown | KY | 40004 | Nelson | KY | Bullitt |
| 65631 | Home Health of Jefferson County | 33221 | 123 Another St. | Louisville | KY | 40206 | Jefferson | KY | Hardin |

700

In this case, "Home Health of Jefferson County" only covers Jefferson (it's physically located there) and Hardin - so it simply needs the Coverage State/County columns filled out. "Sample DME" on the other hand covers several counties, so we had to add lines for each county - all the grey fields should be identical, only the Coverage information should be different.

Entering Data into the Hospitals Bulk Add Forms 950

Hospital Specialties
- ✓ Acute Inpatient Hospitals
- ✓ Inpatient Substance Abuse
- ✓ Durable Medical Equipment
- ✓ Inpatient Psychiatric Facility Services
- ✓ Occupational Therapy
- ✓ Orthotics and Prosthetics
- ✓ Outpatient Dialysis
- ✓ Outpatient Infusion/Chemotherapy
- ✓ Outpatient Mental Health
- ✓ Outpatient Substance Abuse
- ✓ Physical Therapy
- ✓ Speech Therapy
- ✓ Surgical Services (Outpatient or ASC)

Using the drop-down selector, choose the State, Hospital name, and applicable Specialty for the provider. If the hospital offers multiple specialties each will need to show on a separate line. Data for new providers can be updated in the green cells, using the same instructions for updating C3 facilities Medicare bed count must be completed for Inpatient Substance Abuse Services.

Entering Data into the Medical Facilities Bulk Add Form

Button used to upload the contents of the displayed worksheet only to the HSD database for display in the C3 Tool.

Input all data for new providers into the green cells, using the same instructions used in the Practitioner form instructions on slides 17 - 22. All fields, including NPI, Medicare ID (CCN), and Bed Count are required, with the exception of the Optional Notes / Comments field.

If Errors Exist on the Filing...

If the approval was accepted, it will be noted in the Approval Status area.

If the approval was not accepted, you will receive the message above (if all errors have not been corrected for all providers). Click the "OK" button.

Error: Filing errors must be fixed before approval

FIG. 30

MED HSD 2011 - VP Counties by Spec

- High Level summary of overall gaps
- Filter Options
  - -- Yellow - Filter by product (PPO, PFFS, HMO)
  - -- Green - Filter by Network VP
- Columns
  - -- HSD Specialty
  - -- Total Counties - Total counties being filed for the product/ NVP combination
  - -- Passing Counties - CMS adequacy met (either green or light green)
  - -- Gap Counties - All counties not meeting CMS Adequacy (Salmon and white counties)
  - -- Possible Exception Req - Counties with no AMA/ SMG available providers listed (white counties)
  - -- Net Gap Counties - Counties with AMA/SMG available providers listed (salmon counties)

| Medicare HSD - Gap Reports - Counties by Specialty | | | | | |
|---|---|---|---|---|---|
| Product | PPO | | | | |
| Network VP | (All) | | | | |
| HSDSpecDesc | Total Counties | Passing Counties | Gap Counties | Possible Exception Req | Net Gap Counties |
| Primary Care | 573 | 284 | 289 | 124 | 165 |
| Allergy & Immunology | 573 | 355 | 218 | 142 | 76 |
| Cardiac Surgery | 573 | 269 | 304 | 304 | 0 |
| Cardiology | 573 | 375 | 198 | 116 | 82 |
| Chiropractic | 573 | 455 | 118 | 118 | 0 |
| Dermatology | 573 | 361 | 212 | 89 | 123 |
| Endocrinology | 573 | 277 | 296 | 251 | 45 |
| ENT/Otolaryngology | 573 | 414 | 159 | 159 | 0 |
| Gastroenterology | 573 | 327 | 246 | 122 | 124 |
| General Supply | 573 | 395 | 178 | 40 | 138 |
| Gynecology, OB/GYN | 573 | 461 | 112 | 112 | 0 |
| Infectious Diseases | 573 | 277 | 296 | 155 | 141 |
| Nephrology | 573 | 373 | 200 | 90 | 110 |
| Neurology | 573 | 338 | 235 | 107 | 128 |

FIG. 32

MED HSD 2011 - VP Spec by Counties

| Medicare HSD - Gap Reports - Specialty by Counties | | | | | | | | | | | |
|---|---|---|---|---|---|---|---|---|---|---|---|
| Spec | (All) | | | | | | | | | | |
| Product | NetworkVP | StatCounty | | FromCo | PFFS | Total Specialties | Passing Specialties | Tot Gap Specialties | Possible Exception Req | Ctrct Gap Specialties | ExBand | GapBand | TotBand |
| PPO | Name Sample | IN | WASHINGTON | 18175 | 181 | 181 | 181 | 181 | 181 | 2 | 6-15 | 6-15 | 30+ |
| | | | SCOTT | 18143 | 64 | 64 | 64 | 64 | 64 | 0 | 1-5 | 1-5 | 30+ |
| | | KY | BARREN | 21009 | 388 | 388 | 388 | 388 | 388 | 0 | 1-5 | 1-5 | 30+ |
| | Another Name | AR | ASHLEY | 05003 | 16 | 16 | 16 | 16 | 16 | 1 | 6-15 | 6-15 | 30+ |
| | | | BRADLEY | 05011 | 14 | 14 | 14 | 14 | 14 | 0 | 6-15 | 6-15 | 30+ |
| | | | CLAY | 05021 | 344 | 344 | 344 | 344 | 344 | 0 | 6-15 | 6-15 | 30+ |
| | | | CRAIGHEAD | 05031 | 467 | 467 | 467 | 467 | 467 | 0 | 6-15 | 6-15 | 30+ |
| | | | FAULKNER | 05045 | 172 | 172 | 172 | 172 | 172 | 7 | 16-30 | 16-30 | 16-30 |
| | | | GREENE | 05055 | 764 | 764 | 764 | 764 | 764 | 0 | 6-15 | 6-15 | 30+ |
| | | | OUACHITA | 05103 | 469 | 469 | 469 | 469 | 469 | 10 | 16-30 | 16-30 | 16-30 |
| | | | POINSETT | 05111 | 32 | 32 | 32 | 32 | 32 | 0 | 6-15 | 6-15 | 30+ |
| | | | RANDOLPH | 05121 | 446 | 446 | 446 | 446 | 446 | 0 | 6-15 | 6-15 | 30+ |
| | | | VAN BUREN | 05141 | 396 | 396 | 396 | 396 | 396 | 0 | 1-5 | 1-5 | 30+ |
| | | KS | JACKSON | 20085 | 27 | 27 | 27 | 27 | 27 | 0 | 30+ | 30+ | 6-15 |
| | | | MARSHALL | 20117 | 10 | 10 | 10 | 10 | 10 | 8 | 6-15 | 6-15 | 30+ |
| | | | MONTGOMERY | 20125 | 41 | 41 | 41 | 41 | 41 | 5 | 6-15 | 6-15 | 30+ |
| | | | BROWN | 20013 | 5 | 5 | 5 | 5 | 5 | 2 | 1-5 | 1-5 | 30+ |
| | | | ATCHISON | 20005 | 29 | 29 | 29 | 29 | 29 | 4 | 6-15 | 6-15 | 30+ |
| | | | DONIPHAN | 20043 | 16 | 16 | 16 | 16 | 16 | 10 | 16-30 | 16-30 | 16-30 |
| | | | GEARY | 20061 | 141 | 141 | 141 | 141 | 141 | 8 | 16-30 | 16-30 | 16-30 |
| | | | JEFFERSON | 20087 | 29 | 29 | 29 | 29 | 29 | 4 | 6-15 | 6-15 | 30+ |
| | | | LYON | 20111 | 16 | 16 | 16 | 16 | 16 | 4 | 16-30 | 16-30 | 16-30 |

- High Level summary of gaps by county
- Filter Options
  - Green - Filter by Specialty
- Columns - Same as on previous report
  - Plus
    - ExBand - Grouping of exception request gaps by county (white counties)
    - GapBand - Grouping of available providers gaps by county (salmon county)
    - TotBand - Grouping of total gap specialties by county

Figure 34:
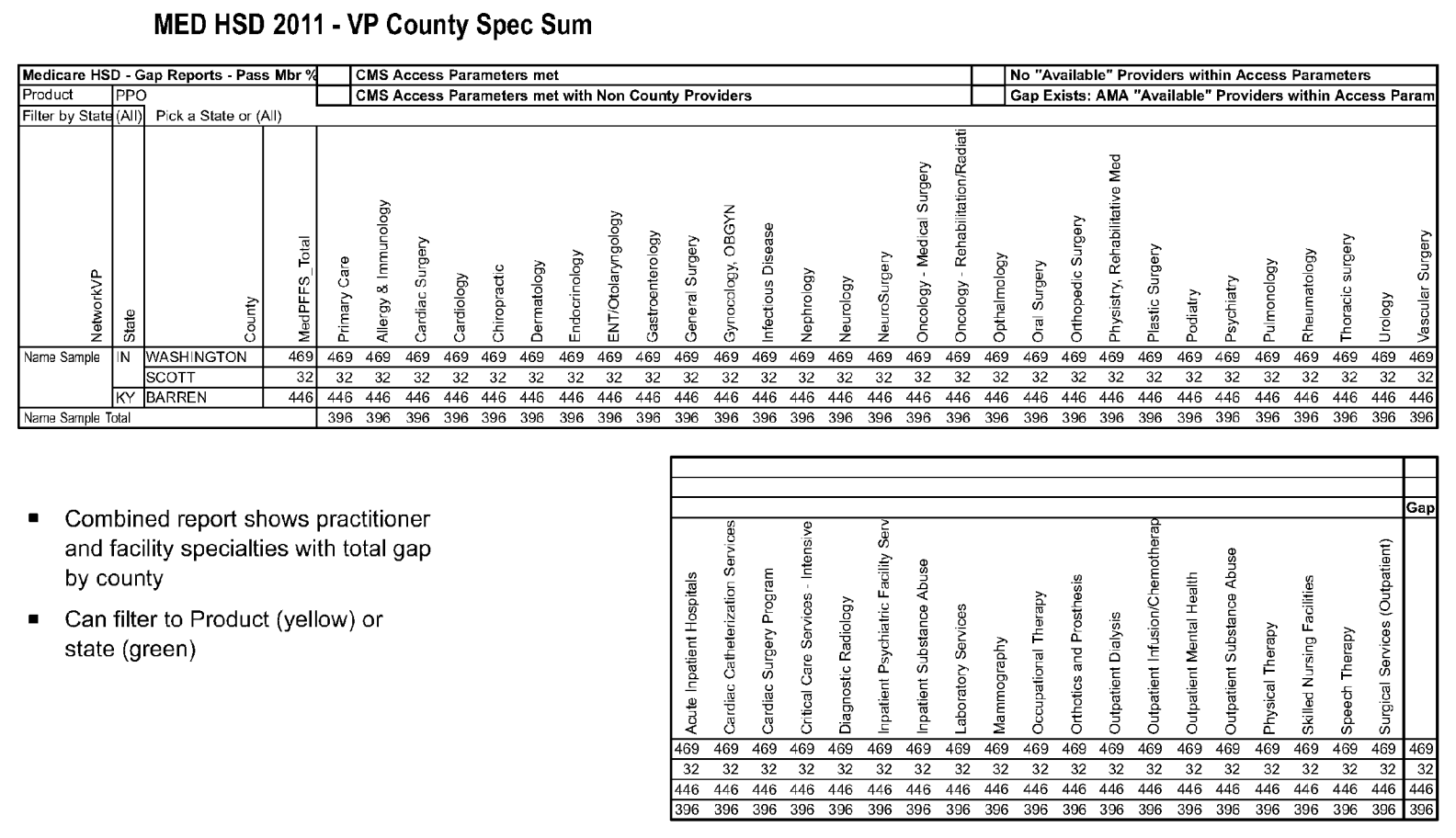

- Combined report shows practitioner and facility specialties with total gap by county
- Can filter to Product (yellow) or state (green)

MED HSD 2011 - County Spec Detail

| PPO | ← Pick a Product |
| --- | --- |
| KS | ← Pick a State |
| MARSHALL | ← Pick a County |
| Gastroenterology | ← Pick a Specialty |

| Get Data | ← Click GetData |
| --- | --- |

Medicare HSD - Gap Reports - Provider Details by State, County, Specialty
These Providers who are within the Required Distance from the CMS Member or Sample and will help increas the Pass %
"AMA" Providers are Available Providers based on the AMA data, "COM" are Providers to the Competitor's Network
"County" Providers are Contracted Providers within County, "SUPPL" are Contracted Supplemental Providers from surrounding counties

| | | % of Members satisfied by Providers meeting minimum required distance | | |
| --- | --- | --- | --- | --- |
| | | In County | In County and Supplemental | In County, Suppl and AMA Avail |
| CMS Members | | 0.0% | 74.0% | 100.0% |
| Total | 147 | | | |

| DistReq | FoundIn | ProvCounty | ProviderName | ProviderAddLineAll | ProvCity | ProvState | ProvZipCode | ProvLat | ProvLong | AvgDistance | Importance |
| --- | --- | --- | --- | --- | --- | --- | --- | --- | --- | --- | --- |
| | 60 AMA | RILEY | First Name, MD | 123 Hylan Heights Rd. | Manhattan | KS | 66502 | 38.182 | -96.853 | 34.6 | 25.2% |
| | | | Second Name, MD | 1234 Hylan Heights Rd. | Manhattan | KS | 66502 | 38.182 | -96.853 | 34.6 | 25.2% |
| | | RILEY | Third Name, MD | 4321 Hylan Heights Rd. | Manhattan | KS | 665022812 | 38.182 | -96.853 | 34.6 | 25.2% |
| | | | Fourth Name, MD | 4321 Hylan Heights Rd. | Manhattan | KS | 665022813 | 38.182 | -96.853 | 34.6 | 25.2% |
| | | Pawnee | Fifth Name, MD | 600 Lake | Pawnee City | NE | 68502 | 38.182 | -96.853 | 34.6 | 25.2% |
| | | Gage | Sixth Name, MD | 123 Hylan Heights Rd. | Beatrice | NE | 688805432 | 38.182 | -96.853 | 34.6 | 25.2% |
| | | | Seventh Name, MD | 123 Hylan Heights Rd. | Beatrice | NE | 688805432 | 38.182 | -96.853 | 34.6 | 25.2% |
| | | | Eighth Name, MD | 123 Hylan Heights Rd. | Beatrice | NE | 688805432 | 38.182 | -96.853 | 34.6 | 25.2% |
| | | | Ninth Name, MD | 123 Hylan Heights Rd. | Beatrice | NE | 688805432 | 38.182 | -96.853 | 34.6 | 25.2% |
| | | Johnson | Tenth Name, MD | 282 High St. | Techumseh | NE | 688809999 | 54.182 | -96.853 | 54.3 | 25.2% |
| | | | Eleventh Name, MD | 282 High St. | Techumseh | NE | 688809999 | 54.182 | -96.853 | 54.3 | 25.2% |
| | | Richardson | Twelfth Name, MD | 2307 Baraeda St. | Falls City | NE | 688809999 | 38.182 | -96.853 | 34.6 | 25.2% |
| | | NEMAHA | Thirteenth Name, MD | 2822 13th St. | Auburn | NE | 688801234 | 38.182 | -96.853 | 34.6 | 25.2% |
| | | SHAWNEE | Fourteenth Name, MD | 4321 Hylan Heights Rd. | Manhattan | KS | 665022812 | 38.182 | -96.853 | 34.6 | 25.2% |

- Must select an option in all yellow boxes and click - "Get Data"
  – Product
  – State
  – County
  – Specialty
- Report drills down to show % meeting access-
- AvgDist - Shows the average proximity of the provider to all members within the county
- Importance - Shows the estimated % of Members who would meet access based on the address listed
- Found In - Look for AMA or Comp to show providers list via AMA or in a competitors network that are not par for the product in question.

FIG. 35

Editable Fields on C3 Practitioners

Request Submitted?: Select "Y" or "N" to note if a request has been emailed to the Medicare Network Strategy Team. If the term process has not been initiated, follow the standard SPOE process.

Scroll to see additional fields

FIG. 36

Fallout for Both C3 Practitioners and C3 Facitlities

| | A | B | C | D | D | E | F | G | I | J | J | K | L |
|---|---|---|---|---|---|---|---|---|---|---|---|---|---|
| 1 | SSA Code | Provider Name | | NPI | Specialty Description | Specialty Code | Contract Type | Address | City | State | Zip | Provider Previously Listed? | Contracted Hospital Where Privileged |

Due to occasional PIMS maintenance, providers may be updated in such a way that we cannot match the user updates to the directory data in the C3 Tool. In the unlikely event that this happens, the historical data for the provider in question is added to the fallout tab. If the market sees a provider on the C3 Tool who they have previously worked, they can check the fallout tab to view what they had entered for the provider in previous weeks.

Important Note: If a provider is added to the Fallout tab, it is the owner's (Market, National Ancillary, or LifeSynch) responsibility to copy and paste the data from this tab back to the Provider List tab. Please check this information weekly as the previous week's information will be removed with the next refresh each Tuesday.

FIG. 37

HEALTH SERVICE DELIVERY TABLES SYSTEM AND METHOD

CROSS REFERENCES TO RELATED APPLICATIONS

This application is a continuation of U.S. patent application Ser. No. 12/956,848, filed Nov. 30, 2010, titled HEALTH SERVICES DELIVERY TABLES SYSTEM AND METHOD, now U.S. Pat. No. 8,352,286, issued Jan. 8, 2013, the contents of which is incorporated herein by reference.

FIELD OF THE INVENTION

The present invention relates to systems and methods for compiling health service delivery ("HSD") tables. Specifically, exemplary embodiments relate to a computerized system that accumulates health care provider data, generates HSD tables, analyzes their adequacy, and approves them for filing with The Centers for Medicare and Medicaid Services ("CMS").

BACKGROUND AND SUMMARY OF THE INVENTION

Medicare is a social insurance program financed by the United States government, providing health insurance coverage to people aged 65 and over. Currently, there are three separate Medicare coverage options which are referred to as Original Medicare, Medicare Advantage, and Medicare Supplement plans. Although similar in name, these three coverage options work differently to meet the health care needs of plan participants.

Original Medicare is a fee-for-service plan. In most cases, original Medicare is available to those 65 years of age or older, those with disabilities, and people with End-Stage Renal Disease. The service is divided into categories: Medicare Part A; and Medicare Part B. Medicare Part A covers inpatient care in hospitals including critical access hospitals and skilled nursing facilities (not custodial or long term care). It also helps cover hospice care and some home health care. Certain conditions must be met to obtain these benefits. Medicare Part B covers doctors' services and outpatient care as well as some other medical services that Part A does not cover such as the services of some physical and occupational therapists and some home health care.

Original Medicare provides very basic coverage for medical expenses, so members are still responsible for costs such as deductibles and coinsurance. Medicare Advantage and Medicare Supplement plans provide additional coverage for medical care. These plans give Medicare beneficiaries the option of receiving their Medicare benefits through private health insurance plans instead of through the original Medicare plan. For people that choose to enroll in a Medicare private health plan, Medicare pays the private health plan a specified amount every month for each member. Private plans are required to offer a benefit package comparable to Medicare's and to cover everything Medicare covers, but they do not have to cover every benefit in the same way. Medicare Supplement Plans are standardized with ten levels of coverage from which to choose. These plans are often referred to as "MediGap Insurance." In contrast, Medicare Advantage plans offer more coverage options as they are not standardized and vary greatly from plan to plan.

Medicare Advantage plans are often times referred to as "Part C" plans. A private company wishing to offer a Medicare Advantage plan in a given county must create and submit a filing package for submission to CMS for approval. There are annual deadlines for the submission of these filing packages, also referred to as Part C applications. Critical in the Part C applications are data compilations known as Health Service Delivery ("HSD") Tables. HSD tables contain information representing provider network adequacy on a county level. All provider data supplied on HSD tables is carefully reviewed by CMS and is a key factor in the acceptance or rejection of Part C applications. HSD tables permit CMS to determine whether a proposed Medicare Advantage plan meets the Medicare requirements mandated by the federal government.

Historically, the compilation of HSD tables has been a painstaking process. Because of the deadlines set on the filing of Part C applications, completing the detailed HSD tables on time for incorporation into the applications has been an extremely hectic task. There is a need in the art for a computerized system for the accumulation, alteration, and review of HSD table data.

One exemplary embodiment comprises a computerized system comprising at least one database storing health care service provider data and one or more servers where the one or more servers are adapted to receive health care service provider data from a remote computer, send the health care service provider data to the database from storage, receive a request from a remote computer to view health care service provider data that meets selected search parameters, retrieve health care provider data from the one or more databases in accordance with the selected search parameters, and transmit the health care service provider data to the remote computer for viewing. In some exemplary embodiments, the one or more servers sends the health care service provider data to the remote computer where it is populated into a worksheet displayed by the remote computer. In a preferred exemplary embodiment, once the health care service provider data is displayed by the remote computer, a system user may review the data and cause amendments to be made to the data stored in the database. In one example, a system user causes changes to be made to data stored in the database by completing an amendment request form that is generated by the system, saving the amendment request form, and then emailing the amendment request form to a reviewing body that sends the amended data to the database.

In some exemplary embodiments, one or more servers of the system runs a set of integrated tools that permit system users to view health care facility and health care practitioner data on a remote computer, cause amendments to be made to the data stored in the database, add health care facility and practitioner data to the database, review health care provider data that has been stored in the database in the format in which it will be filed with CMS (a "final file format"), approve displayed final files for filing, and analyze the health care provider data within final files to determine whether it satisfies CMS requirements.

BRIEF DESCRIPTION OF THE DRAWINGS

A better understanding of the disclosed embodiments will be obtained from a reading of the following detailed description and the accompanying drawings wherein identical reference characters refer to identical parts and in which:

FIG. 3 shows a screenshot of an exemplary embodiment of a practitioner worksheet comprising a "Get Providers" icon selection by which a system user may cause search parameter fields to be displayed on his or her remote computer;

FIG. 5 shows a screenshot of an exemplary embodiment of a practitioner worksheet after it has been populated with health care provider data from the database;

FIG. 7 shows a screenshot of an exemplary embodiment of a practitioner worksheet comprising an "Update Providers" icon which permits a system user to submit updated provider information;

FIG. 8 shows a screenshot of an exemplary embodiment of a service address update form template that may be utilized by the system;

FIG. 9 shows a screenshot of an exemplary embodiment of an owner change request form template that may be utilized by the system;

FIG. 10 shows a screenshot of an exemplary embodiment of a facility worksheet that may be populated with health care provider data by the system;

FIG. 12 shows a screenshot of an exemplary embodiment of a service address update form that may be utilized by the system to request that amendments/updates be made to the address data of a health care providing facility;

FIG. 13 shows a screenshot of an exemplary embodiment of a county coverage update form that may be utilized by the system;

FIG. 14 shows a screenshot of an exemplary embodiment of a county coverage update form containing data for a health care facility that provides coverage for counties other than those in which it is physically located;

FIG. 15 shows a screenshot of an exemplary embodiment of a worksheet that may be utilized by a system user to send practitioner updates to the database;

FIG. 16 shows a screenshot of an exemplary embodiment of a worksheet that may be utilized by a system user to send practitioner updates to the database illustrating how a user may be required to enter at least one contracted hospital for each product;

FIG. 18 shows a screenshot of an exemplary embodiment of a dropdown selection that may be contained in a worksheet that may be utilized by a system user to add hospital data to the database;

FIG. 19 shows a screenshot of an exemplary embodiment of a worksheet that may be utilized by a system user to add practitioner data to the database;

FIG. 20 shows a screenshot of columns that may be included in a worksheet that may be utilized by a system user to add practitioner data to the database;

FIG. 21 shows a screenshot of an exemplary embodiment of a worksheet that may be utilized by a system user to add medical facility data to the database;

FIG. 23 shows a screenshot of an exemplary dropdown selector that may be utilized by the system to prompt system users to select the filing state for which a final file should be generated;

FIG. 24 shows a screenshot of an exemplary dropdown selector that may be utilized by the system to prompt system users to select the CMS Contract Number for which a final file should be generated;

FIG. 25 shows a screenshot of an exemplary embodiment of a "Get Filing Data" icon that may be selected by a system user to prompt the generation of a final file for which search parameters have been selected;

FIG. 26 shows a screenshot of an exemplary final file that has been generated by the system and a notification that may be generated by the system to inform system users that the final file has correctly loaded into the worksheet;

FIG. 27 shows a screenshot of an exemplary embodiment of a final file displaying a file status area and an approval status area;

FIG. 28 shows a screenshot of an exemplary embodiment of a final file displaying filing errors that are contained within the data of the final file;

FIG. 29 shows a screenshot of an exemplary embodiment of a document that may be generated by the system to facilitate the translation of error messages that may be displayed by a final file;

FIG. 30 shows a screenshot of an exemplary message that may be generated by the system if a system user attempts to approve a final file for filing before all errors contained within the data have been corrected;

FIG. 32 shows a screenshot of an exemplary embodiment of a chart that may be generated by the system to assist a system user in assessing the adequacy of a network;

FIG. 33 shows a screenshot of an exemplary embodiment of a chart that may be generated by the system to assist a system user in assessing the adequacy of a network;

FIG. 34 shows a screenshot of an exemplary embodiment of a chart that may be generated by the system to assist a system user in assessing the adequacy of a network;

FIG. 35 shows a screenshot of an exemplary embodiment of a chart that may be generated by the system to assist a system user in assessing the adequacy of a network;

FIG. 36 shows a screenshot of an exemplary embodiment of a practitioner and facility worksheet comprising a column which shows whether or not a request update has been submitted to the system; and FIG. 37 shows a screenshot of an exemplary embodiment of a worksheet that may be utilized by the system to inform system users when data changes were recommended but not made.

DETAILED DESCRIPTION

Figure 1:
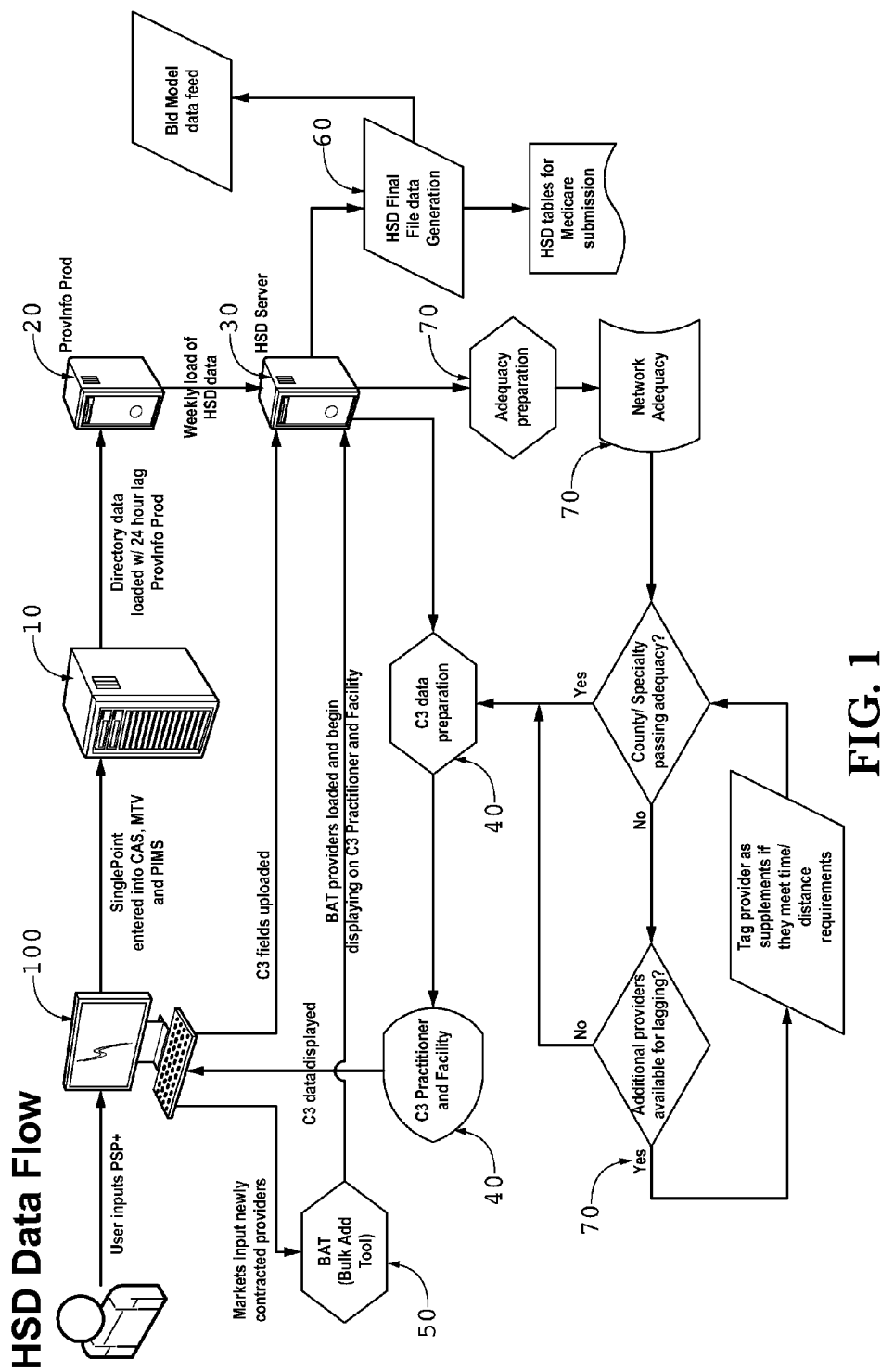
FIG. 1 shows an exemplary embodiment of a computerized system that may be utilized to prepare a filing to CMS for approval of a Medicare Advantage plan.

One exemplary embodiment comprises a method of utilizing a computerized system for preparing, analyzing, and filing a health service delivery ("HSD") table with CMS for the approval of a Medicare Advantage plan. An exemplary embodiment of a computerized system that may be utilized in performing the method is depicted in FIG. 1. As can be seen in FIG. 1, the computerized system may comprise a first server 10, a second server 20, and a third server 30. In another exemplary embodiment, the system may comprise only one server, two servers, or more than three servers. In the exemplary embodiment shown in FIG. 1, the third server 30 may receive requests from a remote computer 100 to amend health care provider data that is stored within the database, receive health care provider data from a remote computer to add to the database, and receive requests from the remote computer to transmit data from the database for viewing. As shown, the third server 30 may also receive data from the second server 20 for incorporation into the database. Prior to sending data to the third server 30 for incorporation into the database, the second server 20 may receive the data from the first server 10 which received the data from the remote computer 100. Server 10 may allow contract loaders to load providers and their contracts for claims payment and provider directories via a remote computer 100. In some exemplary embodiments, Server 20 creates a daily snapshot of provider directory information including service address, phone number, hospital affiliations, and practice information. The third server 30 may run a variety of integrated tools. For example, the third server may run a C3 Practitioner and Facility Tool 40, a Bulk Add Tool 50, a Final File Review Tool 60, and a Network Adequacy Tool 70 as is shown in the exemplary embodiment of FIG. 1.

In a preferred exemplary embodiment, a database storing health care provider data may be accessed by one or more servers that are in communication with at least one remote computer. Communication with more than one remote computer may permit numerous system users to have access to the health care provider data stored in the database, analyze the data, cause amendments to be made to the data, and utilize the data to finalize HSD tables that are filed with CMS for the approval of a Medicare Advantage plan.

In one exemplary embodiment, the computerized system comprises at least one database storing health care provider data and one or more servers in which the one or more servers are adapted to:
  receive search parameters from a remote computer where the search parameters define a targeted set of health care service providers,
  retrieve health care service provider data from the database where the provider data retrieved is in compliance with the search parameters received from the remote computer,
  send the provider data to the remote computer for viewing in a worksheet format,
  receive a request to amend the provider data from the remote computer,
  generate at least one update request form template in response to the amendment request received from the remote computer;
  send the update request form template to the remote computer for viewing and completion;
  receive a command to amend the data stored in the database;
  amend the data stored in the database in response to the received command;
  receive a request from a remote computer to add provider data to the directory system;
  send the provider data to the directory system for storage;
  receive search parameters from a remote computer where the parameters comprise a product ID, a filing state ID, and a CMS contract ID;
  retrieve data from the database where the retrieved data is in compliance with the product ID, filing state ID, and CMS contract ID search parameters;
  transmit the retrieved data to the remote computer for viewing in a final file format where the final file format is the same format that will be utilized for submission of the data to CMS for approval;
  analyze the provider data within the final files and calculate the percentage of Medicare beneficiaries who have access to a provider given a specific set of parameters; and
  tag providers as supplemental when the analysis of the provider data within the final files shows that the coverage provided within county providers is not sufficient to pass the adequacy measurement required by CMS.

In a preferred exemplary embodiment, the health care provider data stored in at least one database comprises health care practitioner and health care facility data. The database preferably stores the practitioner and facility data with corresponding address data which includes state and county data. The state and county data indicate the state and county in which the practitioner or facility is physically located. Additional data which may be stored in the database corresponding to facility and practitioner data includes HSD specialty data, owner data, term data, county coverage data, and other data that may be utilized to complete an HSD table. In one exemplary embodiment, each health care facility and practitioner included in the database is stored with address data, owner data, term data, HSD specialty data, county coverage data, and may be stored with other data utilized to complete an HSD table.

In one exemplary embodiment, one or more servers of the system runs a set of integrated tools that permit system users to view health care facility and health care practitioner data that has been stored in the database on a remote computer, cause amendments to be made to the data stored in the database, add health care facility and practitioner data to the database, review health care provider data that has been stored in the database in the format in which it will be filed with CMS (a "final file format"), approve displayed final files for filing, and analyze the health care provider data within final files to determine whether it satisfies CMS requirements.

In preferred exemplary embodiments, an integrated set of tools executing on one or more servers of the system provides for the assembly, review, and analysis of HSD tables that will be filed with CMS. In one exemplary embodiment, the system comprises a C3 Practitioner and Facility Tool, a Bulk Add Tool, a C3 Final File Viewer tool, and a Network Adequacy Analysis Tool. The tools may execute on one or more servers of the system and in some exemplary embodiments at least one of the system's tools may execute on multiple servers. In a preferred exemplary embodiment, each of the system's tools may be utilized to access the database. Some tools may be able to retrieve health care provider data from the database and send it to a remote computer for viewing while other tools may only be able to send new health care provider data to the database.

In one exemplary embodiment, one or more servers of the system may receive a request from a remote computer to view health care provider data stored in the database in accordance with a set of search parameters that have been selected by a system user. The one or more servers may process the received search parameters and retrieve health care provider data from the database in accordance with those search parameters and send the data to the remote computer for viewing. In a preferred exemplary embodiment, the data sent to the remote computer is populated into a displayed worksheet that permits system users to view the data in table form, review the data, and cause amendments to be made to the data.

In some embodiments, system users may be limited in the ways they may cause amendments to the displayed data to be made.

In one exemplary embodiment, a C3 Practitioner and Facility Tool executing on one or more servers of the system may permit system users to enter search parameters into a remote computer, send the search parameters to the server, cause the server to retrieve health care service provider data from the database in compliance with the received search parameters, and receive the health care service provider data at the remote computer for viewing in a table form. The system user utilizing the C3 Practitioner and Facility Tool ("C3 Tool") may be a contractor of a private company that is applying to offer a Medicare Advantage plan. The C3 Tool may permit the system user to cause amendments to be made to the health care service provider data that is stored in the database.

Figure 2:
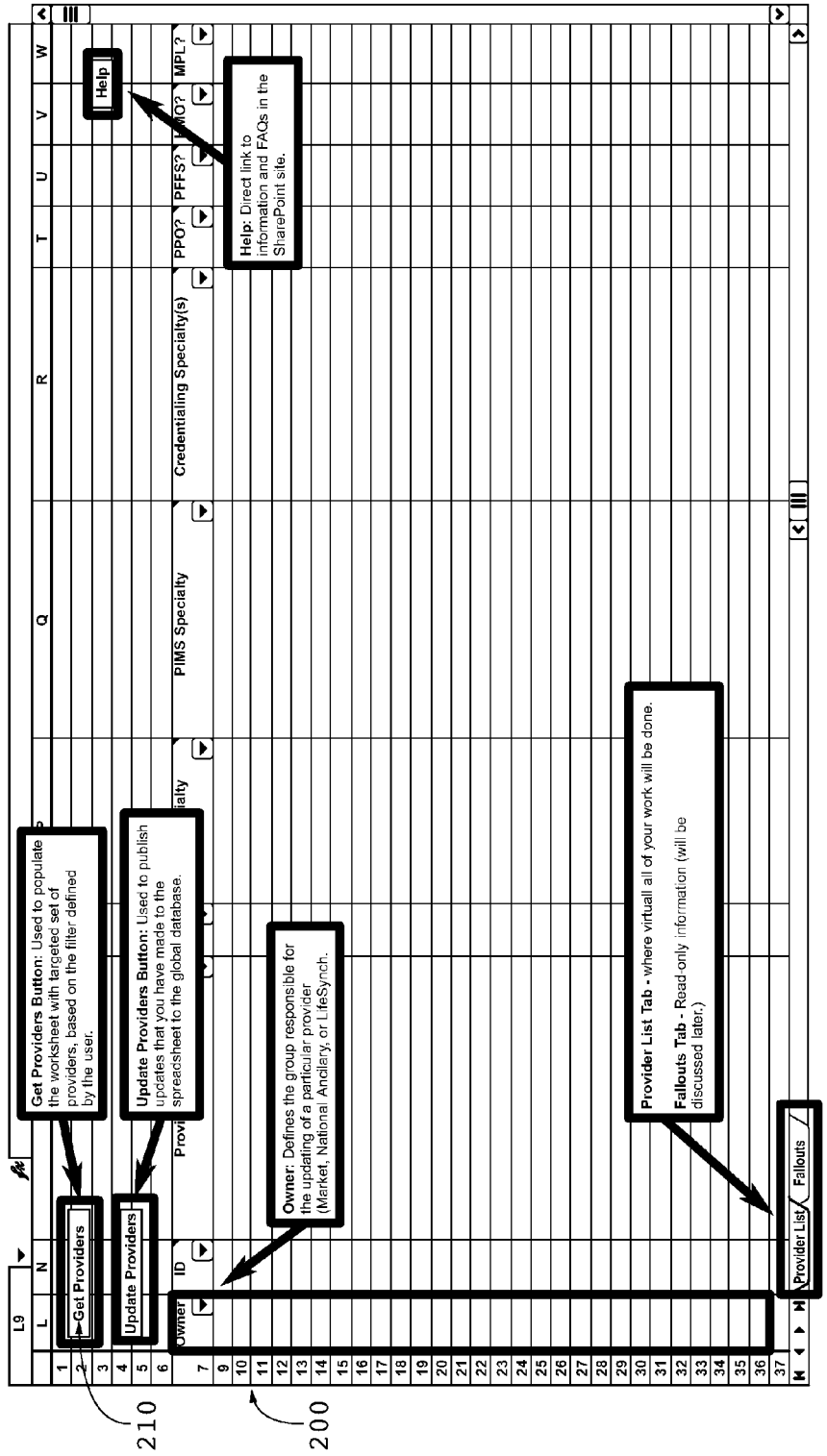
FIG. 2 shows a screenshot of an exemplary practitioner worksheet that may be utilized by the system.
Figure 3:
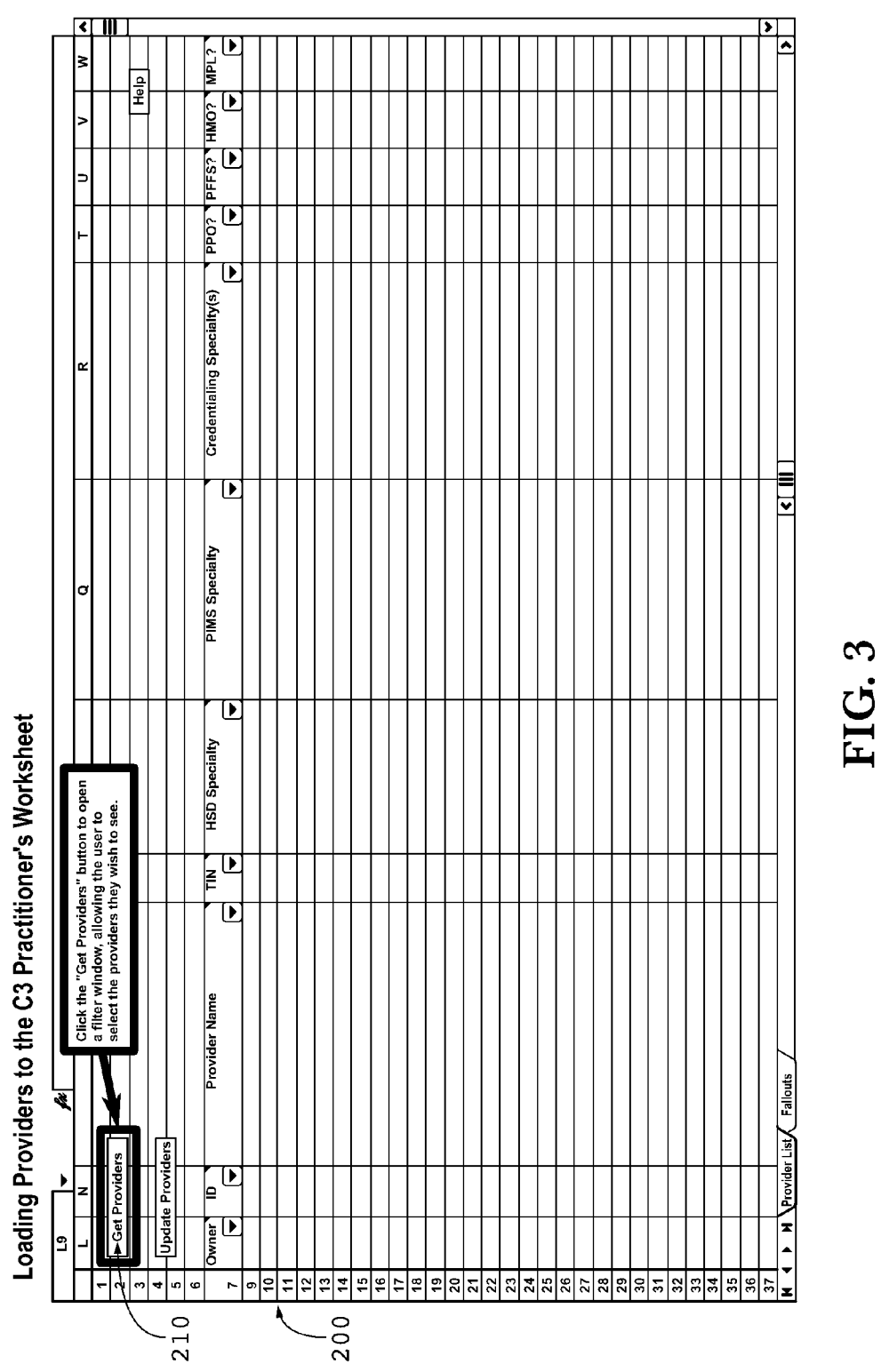

In a preferred exemplary embodiment, the C3 Tool of the system may be utilized to load provider data into practitioner worksheets as well as into facility worksheets viewed on a remote computer. In one example, the system user utilizes the C3 Tool to load provider data from the database into a practitioner worksheet that is viewed by the user on a remote computer. FIG. 2 shows an exemplary embodiment of a practitioner worksheet 200 which may be populated with health care provider data by the C3 Tool. The C3 Tool may load the provider data into the practitioner worksheet based on search parameters entered by the system user. In a preferred exemplary embodiment, the process of loading practitioners into a practitioner worksheet is initiated when a system user selects an icon (such as a "Get Provider" icon) displayed by the remote computer. FIG. 3 shows an exemplary embodiment of a "Get Provider" icon 210 that may be displayed by a remote computer. Once the "Get Provider" icon has been selected by a user, a variety of search filters may be displayed by the remote computer for viewing and selection.

Figure 4:
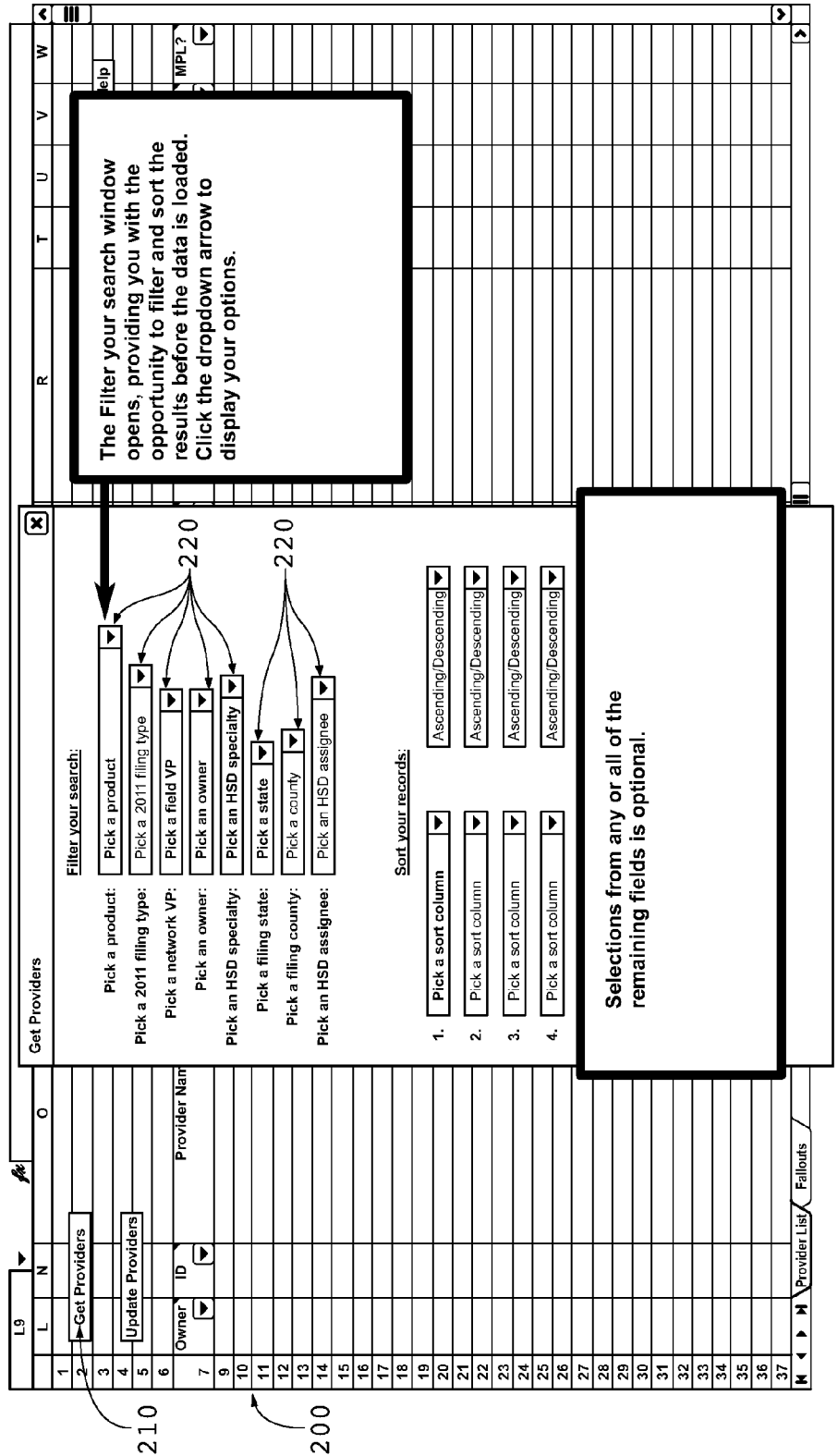
FIG. 4 shows a screenshot of an exemplary embodiment of search parameters that may be displayed by a remote computer.

An exemplary embodiment of search filters 220 that may be sent to the remote computer for viewing is shown in FIG. 4. As shown in FIG. 4 the search filters may comprise product type, filing type, network VP, owner, HSD specialty, filing state, filing county, HSD assignee and may further comprise sorting options. In a preferred exemplary embodiment where these search filters are displayed by a remote computer for viewing and selection, a system user must select an option in a displayed "product type" field but selections in all other displayed filter fields are optional and do not have to be completed before the C3 Tool populates the C3 practitioner worksheet. Once a user has selected filters for his or her search, he or she may cause the selected search parameters to be transmitted to the C3 Tool. Once the search parameters are received by the C3 Tool, it may access the database to retrieve health care service provider data in compliance with the search parameters. Once the health care service provider data is received by the C3 Tool, it may send the data to the remote computer for viewing.

Figure 5:
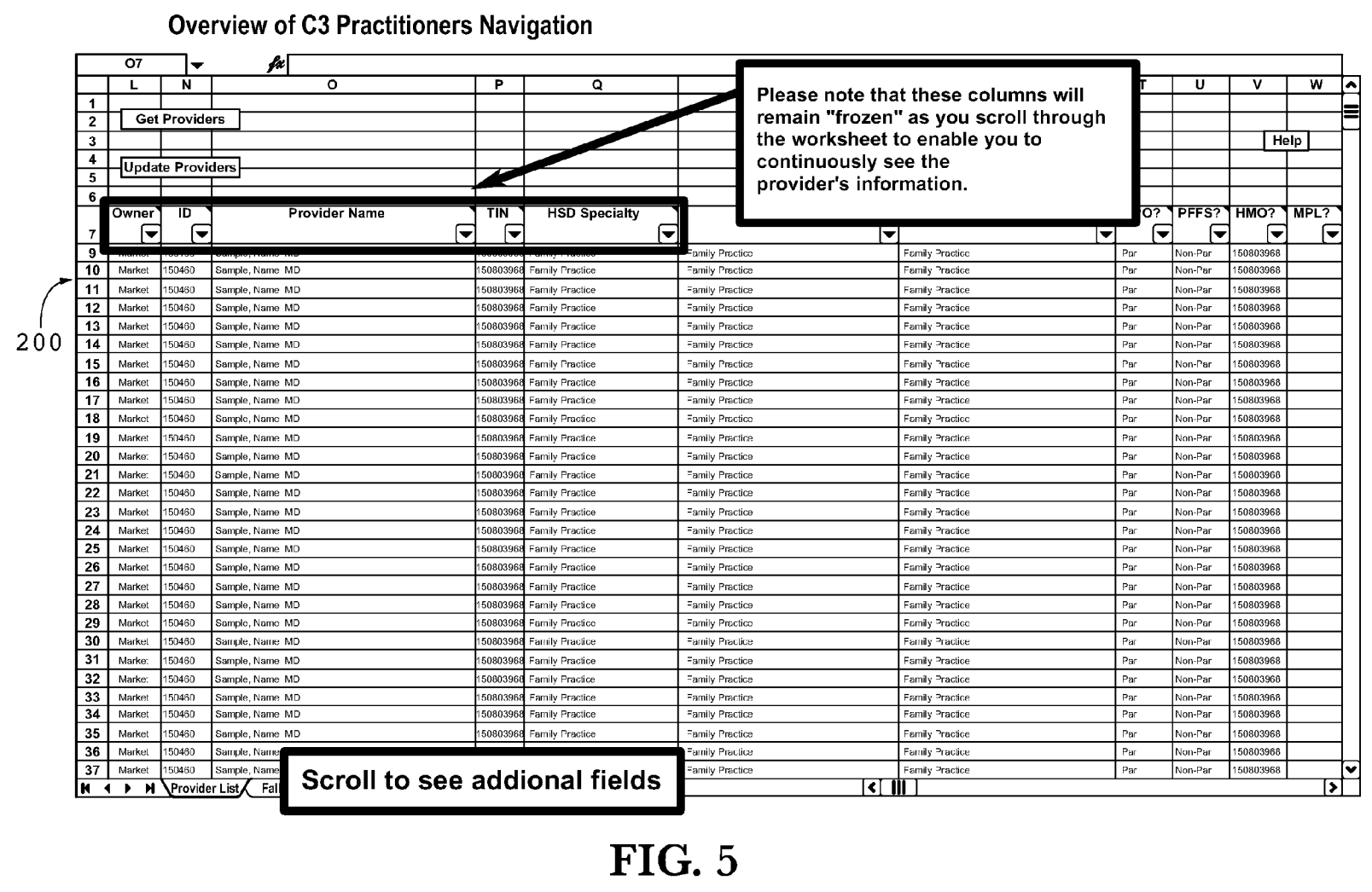

In a preferred exemplary embodiment, health care service provider data is sent to the remote computer for viewing in the form of a practitioner worksheet. Some or all of the columns of the worksheet may correspond to filter fields that were made available to the system user by the C3 Tool. An exemplary embodiment of a practitioner worksheet 200 of health care service provider data that may be sent to a remote computer for viewing is shown in FIG. 5. As shown in FIG. 5 the practitioner worksheet may be in the form of a Microsoft® Excel worksheet. A displayed practitioner worksheet may contain numerous health care practitioner entries where each practitioner is listed in a row on the worksheet. Within each health care practitioner row, there may be numerous columns of data corresponding to a health care practitioner. For example, a row of health care practitioner data may contain data entries for a practitioner's Owner, ID, practitioner name, TIN, the practitioner's HSD Specialty, the practitioner's service address, and other relevant data entries. When a health care practitioner included in the worksheet has more than one service address, HSD specialty, etc. the practitioner may be listed in multiple rows to ensure all the data is shown in the worksheet. In such an exemplary embodiment where the service practitioner has three service addresses for example, a first row may include the data for the first address, while the second and third rows may contain the data for the second and third service addresses respectively.

Figure 6:
FIG. 6 shows a screenshot of an exemplary embodiment of a practitioner worksheet comprising a column that permits system users to select from predetermined types of data amendments that need to be made to the data displayed in the worksheet.

In exemplary embodiments where the C3 Tool sends health care service provider data to the remote computer for viewing in the form of a practitioner worksheet, a system user may be able to cause amendments to be made to the data contained in the worksheet. In a preferred exemplary embodiment, amendments to the worksheet may be made in accordance with a previously defined protocol that may only permit changes to be made to certain portions of the data displayed in the worksheet. For example, a worksheet of health care service provider data may comprise a "Request Type" column and a "Request Submitted" column. The "Request Type" column may permit a user to select from previously defined amendments that may be made to the displayed data. For example, the "Request Type" column may permit a system user to select from four types of amendments: "no amendment request" (which may be depicted in the worksheet as a blank field), "Service Address Update," "Provider Term Error Correction," and "Owner Change." FIG. 6 shows an exemplary embodiment of a worksheet comprising a "Request Type" column 230 that permits a system user to select from four amendment types that may be made to the displayed data. One of the four amendment requests may be selected through a dropdown list made available in the Request Type column.

Figure 7:
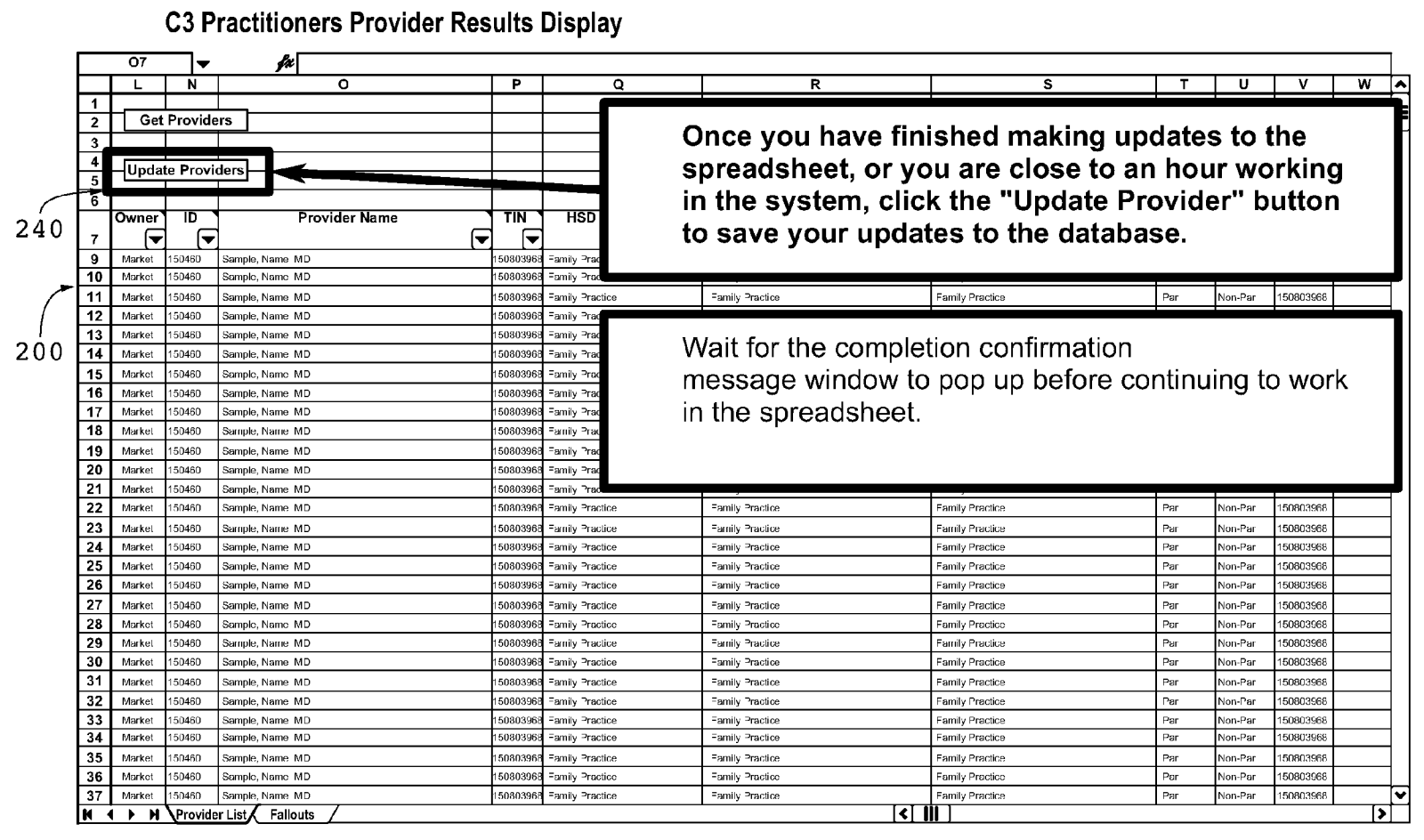

In one exemplary embodiment, a system user scrolls through the list of health care service providers included in a displayed worksheet and for each provider, selects one of the four amendment types he or she wishes to make to the displayed data. It may not be necessary to make a selection for "no amendment request" as that may be the default position of the fields within the "Request Type" column. Once the user has selected a request type for each listed practitioner, he or she may cause the selected requests to be submitted to the C3 tool. In a preferred exemplary embodiment, the requests are submitted to the C3 tool by selecting an "Update Provider" icon. The Update Provider icon 240 may be displayed within a worksheet of health care service provider data as shown in FIG. 7. Once the system user has selected the Update Provider icon, the C3 Tool may process the submitted requests and send corresponding data to the remote computer for viewing. The data may be populated into a form template to be viewed and completed by the system user.

In one exemplary embodiment, a C3 Tool receives requests to amend practitioner data that have been submitted by a system user. Once the requests are received by the C3 Tool, it may process the requests and depending on the requests received, may cause at least one template form to be sent to the remote computer for viewing and to be completed by the system user. When a system user may submit only predefined requests to amend data, the template forms sent to the remote computer for viewing may correspond to the predefined requests. For example, a system user may be able to select from four types of amendments: "no amendment request;" "Service Address Update;" "Provider Term Error Correction;" and "Owner Change." In such an example, the C3 Tool may send up to three different template forms to the remote computer for viewing where one of the forms corresponds to "Service Address Update" requests, one form corresponds to "Provider Term Error Correction" requests, and the third form corresponds to "Owner Change" requests.

In one exemplary embodiment, a system user scrolls through a displayed worksheet that contains data for numerous health service practitioners and submits requests to amend the data listed for some of the listed practitioners. In one example, a system user may submit a "Service Address Update" request for 15 of the listed practitioners, a "Provider Term Error Correction" request for 30 of the listed practitioners, and an "Owner Change" request for four of the listed practitioners. Once the C3 Tool receives the requests, it may send three template forms to the system user's remote computer for viewing. One of the forms, may correspond to the "Service Address Update" requests received by the C3 Tool and the form may contain a list of the 15 practitioners for whom the Service Address Update requests were submitted. Similarly, the template forms that correspond to the "Provider Term Error Correction" and "Owner Change" requests may contain a list of the 30 and four practitioners respectively for whom those requests were submitted by the system user. In summation, the template forms may each contain a list of the practitioners for whom the system user had submitted the corresponding request to amend data.

Figure 8:
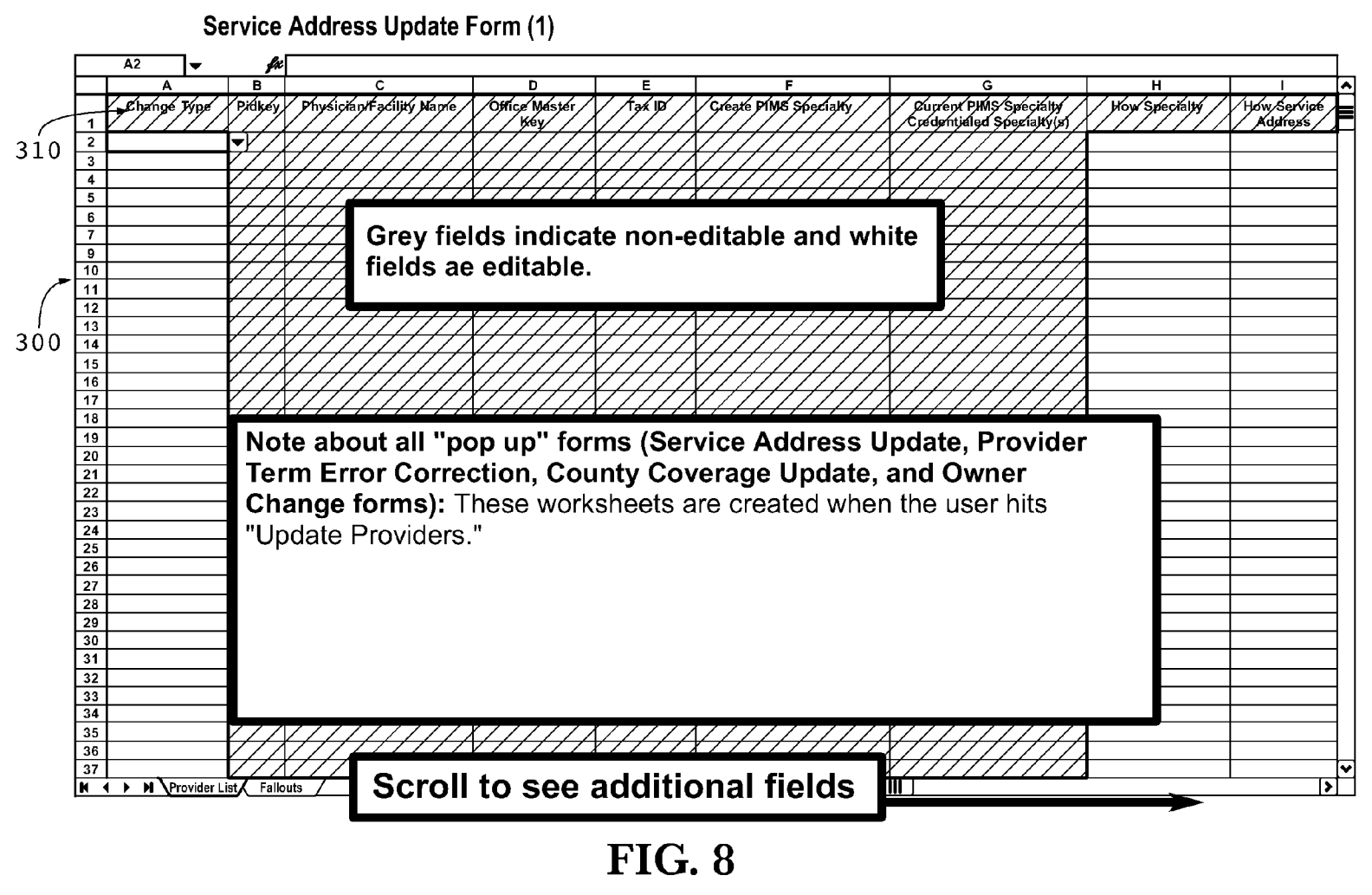

An exemplary embodiment of a viewable template form that may correspond to "Service Address Update" request is shown in FIG. 8. As shown, the template form may be presented as a worksheet such as those that may be assembled in Microsoft® Excel and similar programs. The template form 300 may list all of the health care providers for whom a "Service Address Update" request was submitted to the C3 Tool by the system user. When the template form is presented as a worksheet such as the one shown in FIG. 8, each row of the worksheet may contain data pertaining to a health care service provider for whom a "Service Address Update" request was received. For example, if a system user submitted requests to amend the service address of 45 separate health care practitioners, the corresponding template form worksheet may contain 45 rows where each of those rows contains data pertaining to one of the health care practitioners for whom an address amendment request was submitted.

In the exemplary template form shown in FIG. 8, a system user may make amendments to certain fields of the worksheet but not others. As shown, the white fields may be edited by the system user while the gray fields may not be edited. Data within the gray fields may be pre-populated into the template when the system user selects the "Update Providers" icon. When a system user is working on completing the editable fields of a worksheet template that corresponds to service address update requests, the user may be required to indicate what type of service address update is being requested. As shown in the exemplary embodiment of FIG. 8, the user may indicate the type via a "Change Type" column 310 within the worksheet. In a preferred exemplary embodiment, a dropdown list within a worksheet column permits a system user to select from three types of service address updates: add, update, and term.

In the exemplary embodiment of FIG. 8, a system user may select the "add" type of service address request when there is a need to add an additional service address for the corresponding health care service provider. The system user may then be able to edit an additional field (or additional fields) within the worksheet to contain the new address, city, state, and zip code for the health care provider. The worksheet may comprise a comments section where the system user may enter the phone number corresponding to the service provider's additional address. The system user may also be able to enter the following statement in the comments section: "Please add additional service address to (insert corresponding identifying information for the health care services provider for whom additional address is being submitted)."

Similarly, a system user could select the "Update" type of service address request when the demographic information data listed for a health care service provider needs to be modified. The worksheet may contain editable columns corresponding to "new address," "new group," "new suite number," "new specialty", etc. Depending on the demographic data that needs to be modified for a particular health care service provider, the system user may enter the modified data in the corresponding column. For example, if the health care provider's address is incorrect, the system user may enter the modified address into the "new address column" that corresponds to the health care provider's row on the worksheet. Similarly, the health care provider's group may need to be modified. The system user may enter the correct group for that health care provider within the "new group" column. If the worksheet comprises a comments section, as is preferred, a system user may enter comments regarding the requested modifications in that section.

Finally, in some embodiments a system user may select the "term" type of service address request in the instance that an old office address appears in error. The office for the health care provider may have moved or closed. The "term" type of service address request may also be utilized when an office for a health care service provider appears in duplicates due to slight spelling differences between two data entries (for example, an office may appear twice, once with Saint Petersburg listed as the city, and once with the city provided as St. Petersburg). If the worksheet comprises a comments section, the system user may be able to indicate whether the term request has been made because of a duplicate or an old office address.

The C3 Tool may also generate a form template that corresponds to requests received to correct provider term errors. The form template may permit system users to terminate listed health care service providers from the Medicare network when the provider was deemed in error or a termination single point of entry (SPOE) was previously submitted for the provider in question. The form template may be in the form of a worksheet that lists each of the health care service providers for which a request to correct provider term errors was received. The health care service providers may be listed within the rows of the worksheet. For example, if a system user submitted a request to correct provider term errors for 20 health care service providers, a worksheet may contain 20 rows where each row contains data corresponding to a single health care provider for which a request was received. The system user may be able to complete a field within the worksheet indicating the product to which the term applies. Different product options may be made available for selection by the system user via a dropdown box within a column of the worksheet. A comments section within the worksheet may permit system users to supply additional comments and indicate why the request constitutes an error correction and not a standard termination of a health care services provider from the network.

Figure 9:
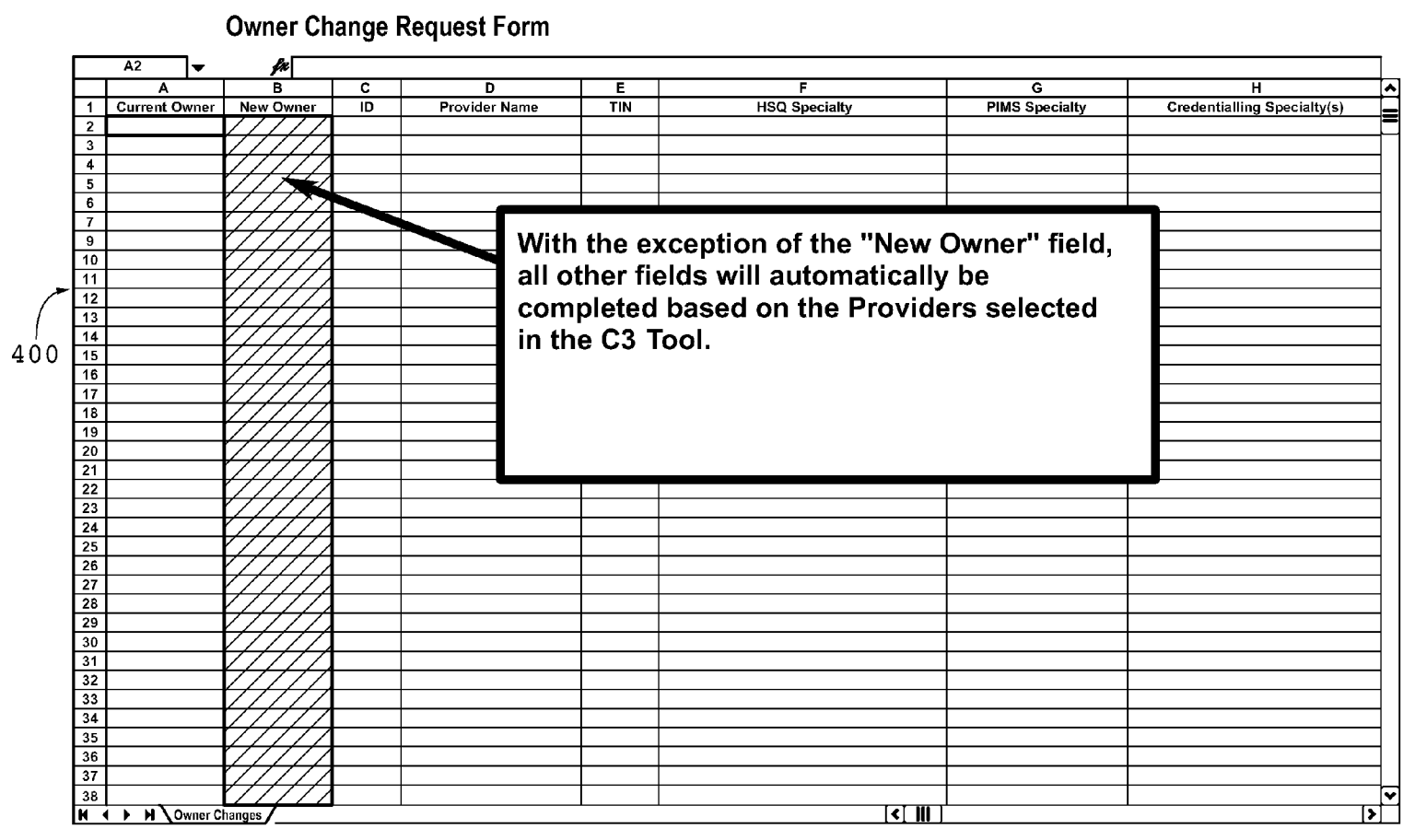

An exemplary template form 400 that may correspond to a received request to change the owner of at least one health care service provider is shown in FIG. 9. As shown, the form may be presented for viewing and completion by a system user as a worksheet. In a preferred exemplary embodiment, all fields of the worksheet are populated for the system user once he or she has submitted his or her request to amend the ownership of at least one health care service provider. The field that the system user may be required to edit is the "new owner" field.

In another exemplary embodiment, a single template form may be sent by the C3 Tool to the remote computer upon receiving requests to amend the data corresponding to health care service providers regardless of the different types of amendment requests that may have been received by the C3 Tool. In such an exemplary embodiment, the single template form may have multiple sections where each section corresponds to a different type of amendment request that has been submitted to the C3 Tool by a system user. Each section may contain a list of the health care service practitioners for whom the corresponding amendment requests were submitted. For example, if a section of the form corresponds to "Owner Change" amendment requests, that section may contain a list of the health care practitioners for whom the system user submitted a request to amend the owner data that was displayed on his or her remote computer.

Figure 10:
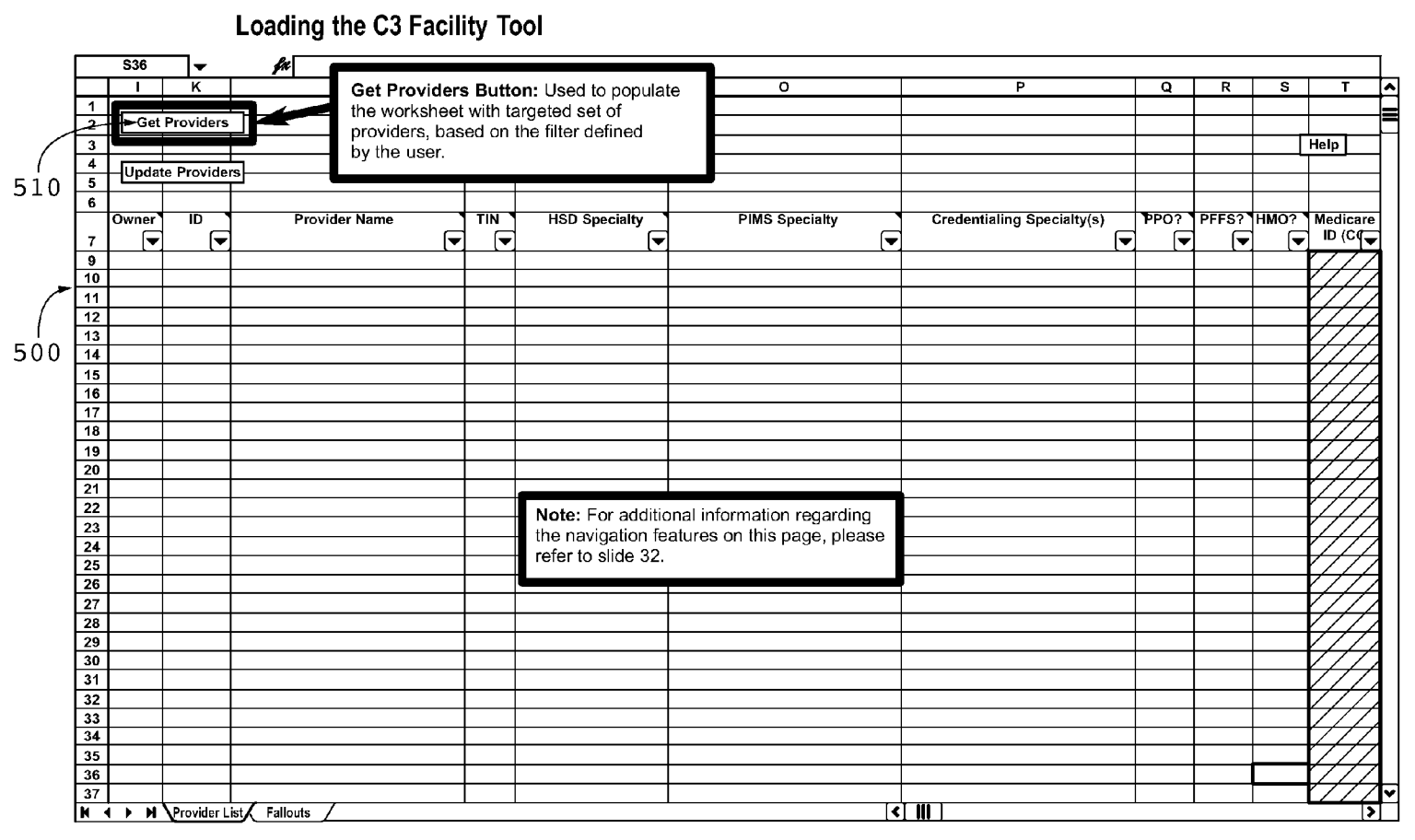
Figure 11:
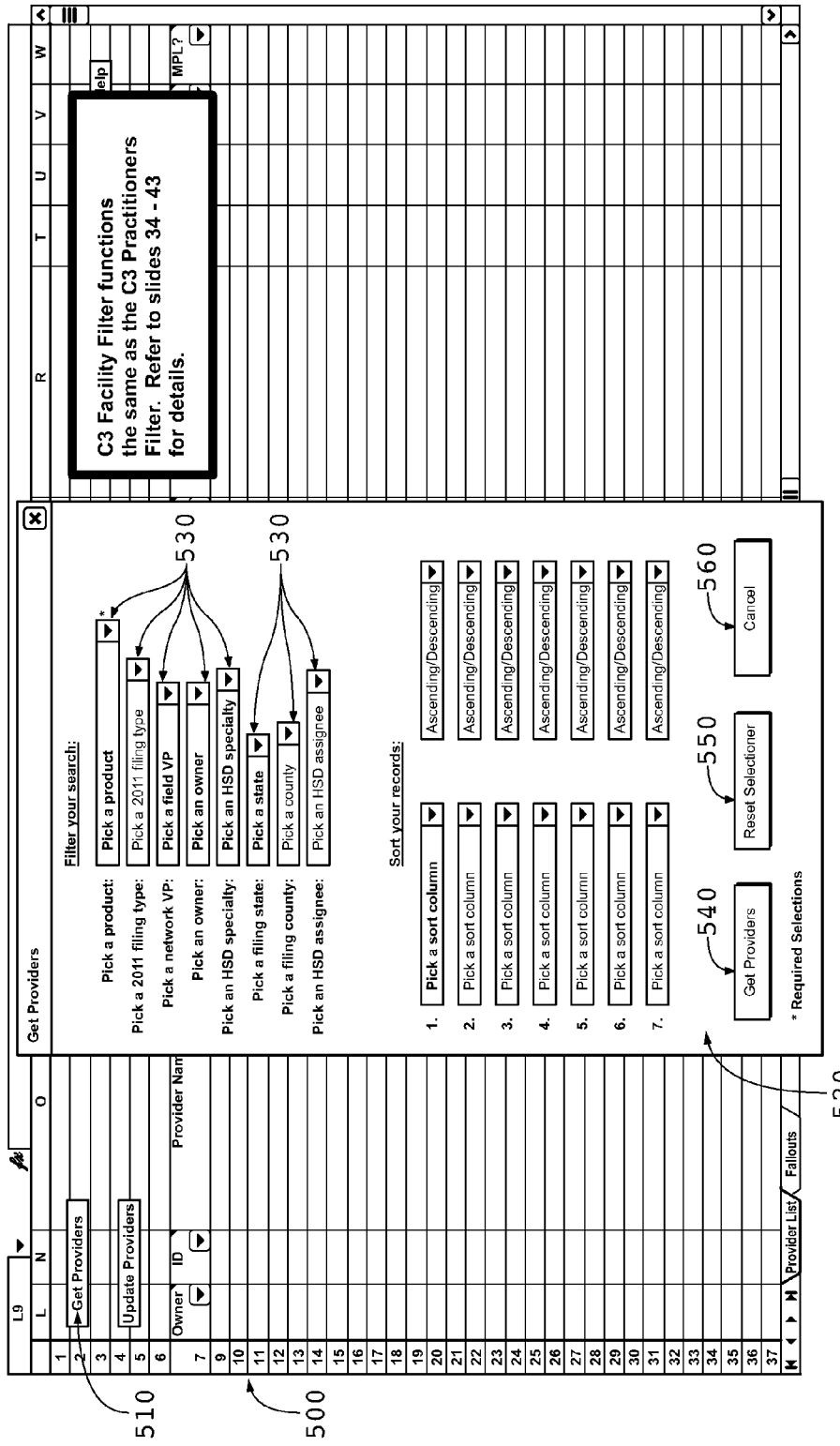
FIG. 11 shows a screenshot of an exemplary embodiment of search parameters that may be displayed within a window by a remote computer.

As was discussed, in a preferred exemplary embodiment, a system user may also utilize the C3 Tool to retrieve and view a facility worksheet where the facility worksheet is populated with health care service provider data from the database based on search parameters that have been entered into the C3 Tool by the system user. An exemplary embodiment of a facility worksheet 500 is shown in FIG. 10. As shown in the FIG. 10 embodiment, the worksheet may contain a "Get Providers" icon 510 which may be selected by the system user. Selecting the "Get Providers" icon may prompt a display of various filters for viewing and selection by the system user. As shown in FIG. 11, the list of Filters may be provided within a window 520 displayed on the screen of the remote computer. FIG. 11 shows an exemplary embodiment of the filters 530 that may be utilized to enter health care provider search parameters into the C3 Tool shown within a window on the screen of a remote computer.

Once the system user has selected desired search filters, he or she may instruct the C3 Tool to populate a facility worksheet. The instruction may be sent to the C3 Tool by selecting an icon displayed in the same window that contains search filter options. As shown in FIG. 11, the window 520 may contain various icons including a "get providers" icon 540, a "reset selections" icon 550, and a "cancel" icon 560. The "get providers" icon may be the icon selection that causes the C3 Tool to populate a facilities worksheet with health care service provider data according to the search parameters that have been selected by the system user. The "reset selections" icon may permit a system user to go back to the default settings of the filters provided by the C3 tool while the "Cancel" icon may permit a system user to cancel a previously submitted "Get Provider" request if for example the request is taking too long to complete.

In some exemplary embodiments, once the C3 Tool has populated a facility worksheet for viewing and editing by the system user, the system user may be able to utilize the facility worksheet to make amendments to health care provider data stored in the database. As was the case with the practitioner worksheets, facility worksheets preferably contain lists of various health care providers that satisfy search parameters that have been entered by the system user. Each row of a facility worksheet may contain data pertaining to a different health care providing facility. If a system user needs to amend the health care provider data shown in a facility worksheet, he or she may have to submit a request to make an amendment. The types of amendments that can be made to the displayed data may be limited. For example, the worksheet may comprise a "request type" column which has a drop-down bar permitting the system user to select from five different amendment types: no amendment request (preferably the default position and indicated by a blank field in the worksheet thus requiring no actual "selection"), "Service Address Update" request, "Provider Term Error Correction" request, "County Coverage Update" request, and "Owner Change" request.

Figure 12:
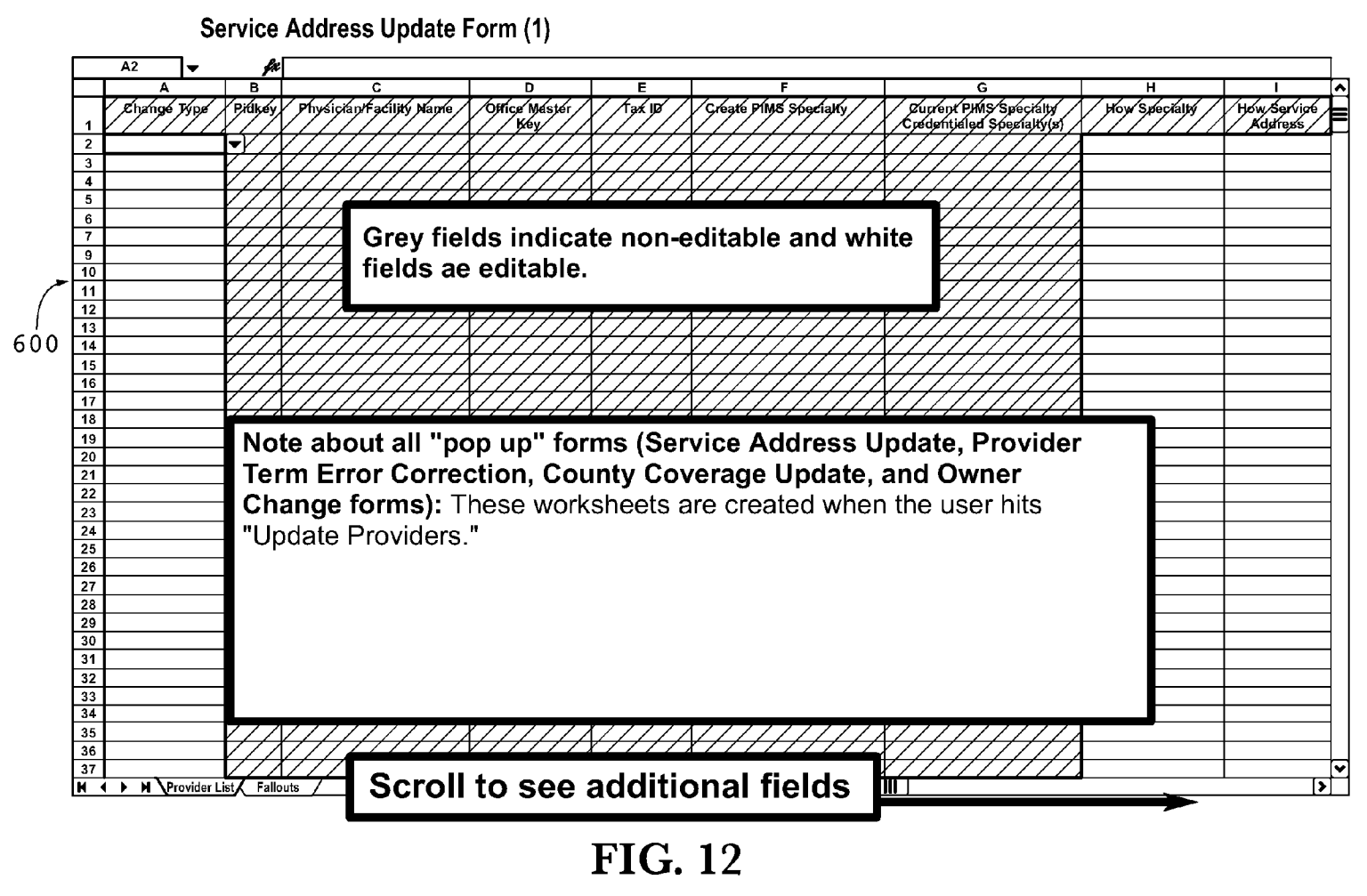

In one exemplary embodiment, once a system user has scrolled through the listed health care providers within a facility worksheet and indicated which data amendment is requested for each of the listed providers, he or she may be able to submit the amendment requests to the C3 Tool for processing. This submission may be completed via the selection of an "Update Providers" icon displayed within the facility worksheet. Once the system user has submitted his or her amendment requests to the C3 Tool, it may populate and send for viewing template forms that correspond to the amendment requests received. As was the case with amendment requests submitted through practitioner worksheets, the C3 Tool may populate separate forms where each form corresponds to an amendment type that has been requested by the user. For example there may be a "Service Address Update" form, a "Provider Term Error Correction" request form, a "County Coverage Update" request form, and an "Owner Change" request form. "Service Address Update" forms, "Provider Term Error Correction" request forms, and "Owner Change" request forms may be configured the same and consequentially utilized in the same manner as those that were generated by the C3 Tool when amendment requests were submitted off of practitioner worksheets. The only difference may be that the data contained within the forms corresponds to health care facilities rather than health care practitioners. In preferred exemplary embodiments, the data that may be entered into these forms by system users is the same despite this difference. FIG. 12 shows an exemplary embodiment of a "Service Address Update" form 600 that may be generated when a system user submits a request to update the address of at least one health care facility listed in a facility worksheet. As can be seen, the form may be substantially identical to that which was prepared by utilizing a practitioner's worksheet shown in FIG. 8.

A facilities worksheet may permit system users to submit a "county coverage update" request. In a preferred exemplary embodiment, once a system user has submitted a request to update the county coverage of at least one health care facility, which may be done by selecting that amendment type from a dropdown bar in a "request type" column in some exemplary embodiments, the C3 Tool may generate a County Coverage Update form template and send the form for viewing at the remote computer. The template may be presented for viewing in the form of a worksheet. In some exemplary embodiments, the County Coverage Update form template permits system users to update the database to indicate that a facility provides services to Medicare beneficiaries located in counties other than the county in which the facility is physically located. In a preferred exemplary embodiment, the county coverage update form template is presented as a worksheet containing only a single row for each provider for which the system user requested a county coverage update.

FIG. 13 shows an exemplary embodiment of a county coverage form template 700 that may be generated by the C3 Tool. In one exemplary embodiment, a county coverage update form template presented as a worksheet comprises a "coverage state" column and "coverage county" column where the columns may be edited by the system user to contain the state and county data (respectively) that corresponds to the county which needs to be added to the facility's coverage. In this exemplary embodiment, if the health care facility for which the county coverage update was requested, covers only one county in addition to the county in which the facility is physically located, the system user may simply need to complete the "coverage state" and "coverage county" fields within the single row. If however, the facility covers more than one county in addition to the county in which it is physically located, the system user may need to provide one row of data per each county covered. FIG. 14 shows an exemplary embodiment of how multiple rows may be utilized by a system user to complete a County Coverage Update form template 700 when a health care facility covers more than one county in addition to the county in which it is physically located. In the exemplary embodiment of FIG. 14, Joe's DME is a health care facility physically located in Nelson county but which additionally covers Marion, Spencer, and Bullitt counties.

In one exemplary embodiment where a C3 tool generates form templates based on requests to update information submitted by a system user, the form templates are populated when the system user selects the "Update Providers" icon displayed within the practitioners or facilities worksheet. For example, a system user may work in the C3 practitioner table from 9 AM to 10 AM on a given day. During that time, the user may request various update options in the "Request Type" column of the worksheet. At 10 AM, the user may select the "Update Providers" icon causing update form templates, containing lists of the health care service providers for whom the user has submitted data update requests, to be generated in the form of Excel spreadsheets. The system user may then enter the necessary information within the form templates and save the template by selecting "file/save as" within the form and then naming and saving the files when prompted. The system user may follow the same process from 10 AM to 11 AM. This time, when the system user selects the "Update Provider" icon, only the providers for which the system user submitted update requests within the 10-11 hour appear within the lists of the form templates generated.

In one exemplary embodiment, once a system user has completed an update form template (for example a "Service Address Update" form, a "Provider Term Error Correction" request form, a "County Coverage Update" request form, or an "Owner Change" request form) in which the form template contains at least one request to amend data within the database of the system, the system user may be able to name and save the form. In some embodiments, the file may be saved on a server accessible by the remote computer. Once saved, the system user may be able to forward the change request form to a reviewing entity via email. The reviewing entity may then cause the database to be updated in accordance with the request to amend data that was contained within the form template file. This procedure may be followed regardless of the type of form request template. In some exemplary embodiments, when an update request form has been emailed for review, the system user may indicate that the request has been submitted within the C3 practitioner or facility worksheet which the system user was working from when the request update form was generated. A column within the practitioner and facility worksheets may permit the system user to indicate whether or not a request update has been submitted as is shown in the exemplary embodiment of FIG. 36.

In one exemplary embodiment, the system indicates when changes to data store in the data base that have been suggested by a system user have not been made. In one exemplary embodiment, the system generates a worksheet that may be accessed by system users where the worksheet shows changes that were recommended to health care provider data stored in the data base that were not actually made to the data. FIG. 37 shows an exemplary embodiment of a worksheet that may be utilized by the system to inform system users when data changes were recommended but not made.

Figure 15:
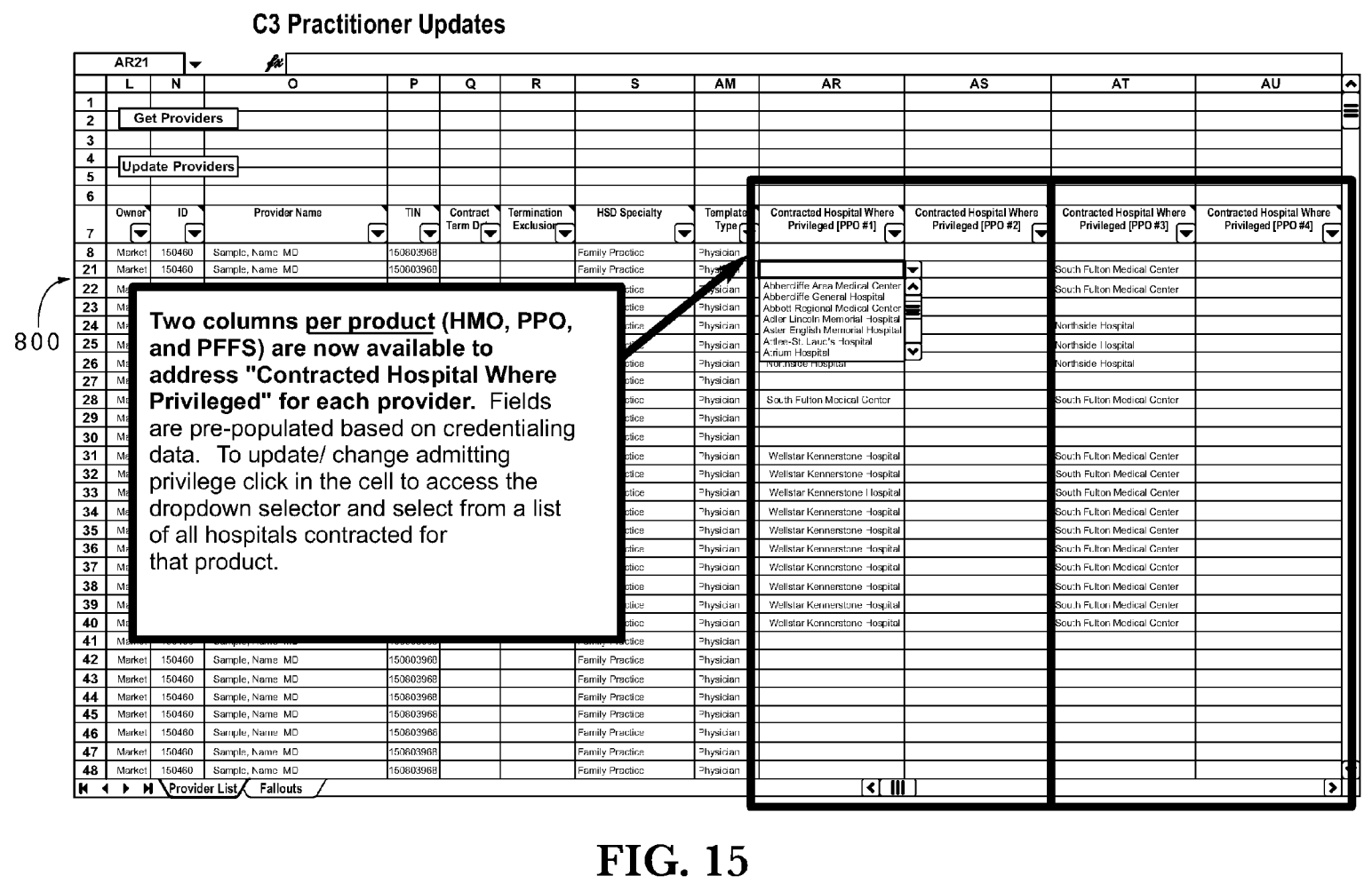

In one exemplary embodiment, a C3 Tool permits users to submit practitioner updates and process changes as well as facility updates and process changes to the database. A system user may be able to submit practitioner updates and process changes to the one or more databases of the system by accessing the C3 Tool through a remote computer, instructing the tool to send search filters for viewing and selection, selecting search parameters and sending them to the C3 Tool, and reviewing and editing practitioner data that has been retrieved from the database and sent to the remote computer for viewing. The C3 Tool may send the practitioner data to the remote computer to be viewed in the form of a worksheet. FIG. 15 shows an exemplary embodiment of a worksheet containing practitioner data 800 that may be edited by a system user. As shown, each row of data within the worksheet may correspond to three different products: an HMO; a PPO; and a PFFS. It may be desirable to include different columns within the worksheet for each product. FIG. 15 shows an exemplary embodiment of a worksheet containing two columns per product. In a preferred exemplary embodiment, fields within the practitioner worksheet are pre-populated by the C3 Tool based on credentialing data stored in the database.

Figure 16:
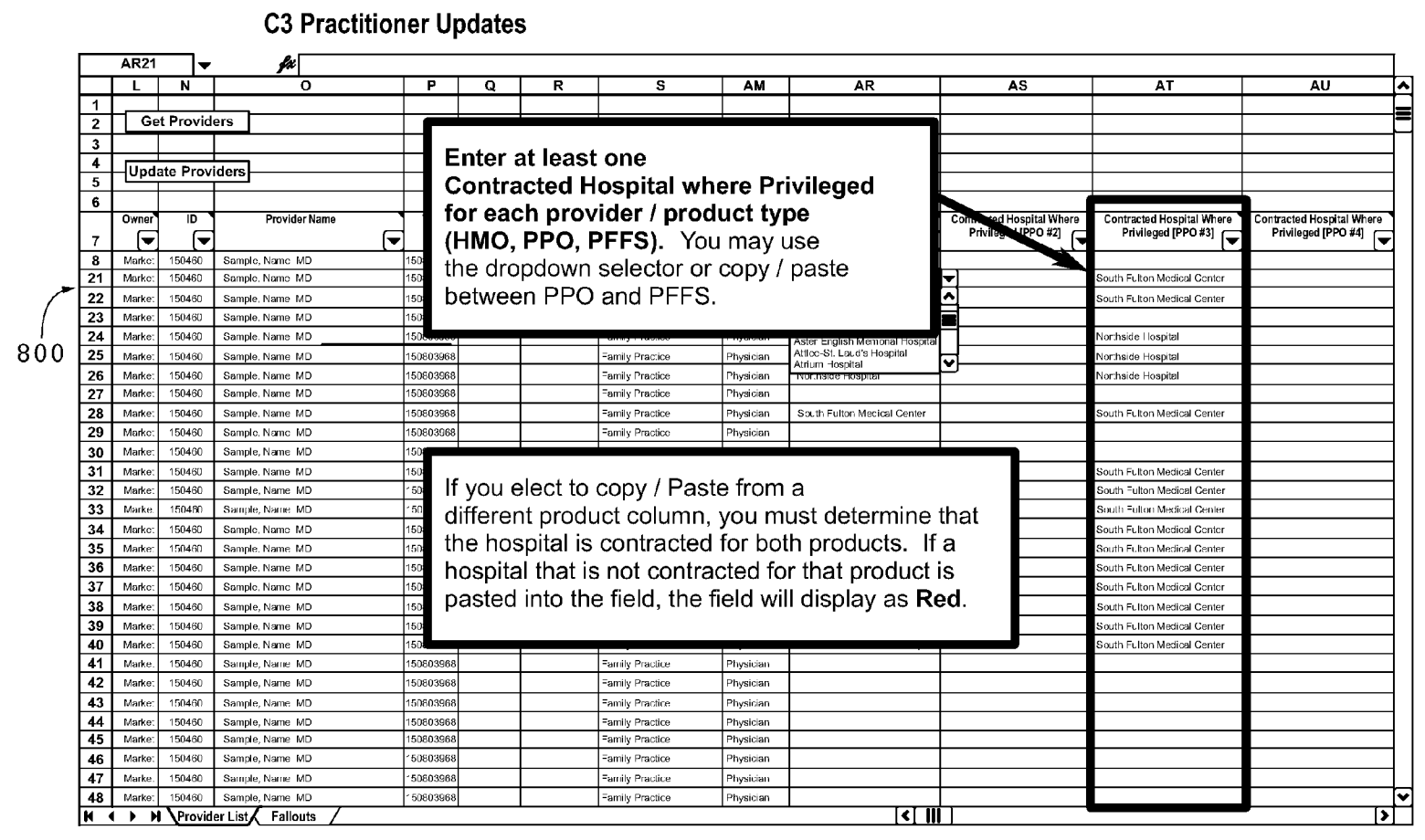

A system user may be able to update/change the data displayed within the worksheet. In one exemplary embodiment, a system user may update/change the admitting privileges of a practitioner listed in a practitioner worksheet by selecting a field of the worksheet within the practitioner's row, accessing a dropdown selector, and selecting from a list of hospitals that have been contracted for the relevant product. In one exemplary embodiment, system users may be asked to enter at least one contracted hospital in which "privileged" for each practitioner/product type is listed in the worksheet. FIG. 16 shows an exemplary embodiment of a worksheet in which a system user enters at least one contracted hospital identifying "privileged" for each product/practitioner. In some exemplary embodiments, a system user may cut data from one column or row within a worksheet and paste it into another column or row. If cutting and pasting data within a worksheet causes incorrect data to be inserted into a field, the field may present the data as red so the system user is aware of the inaccuracy. For example, if a user cuts and pastes data from a "Contracted Hospital Where Privileged" for the PPO #1 product and pastes it into the "Contracted Hospital Where Privileged" for the PFFS #1 product column, and a hospital that was contracted for the PPO#1 product was not contracted for the PFFS#1 product, the worksheet may display the hospital entry within the PFFS#1 column as red. In a preferred exemplary embodiment, once a system user has entered the practitioner updates and processed changes into the worksheet, they may be submitted to the database of the system. In one exemplary embodiment, the system user selects an "update provider" icon displayed on the practitioner worksheet that causes the C3 Tool to send the practitioner updates and process changes that have been made to the database for storage.

A system user may also be able to utilize the C3 Tool to submit facility updates and process changes to the data housed in the database. In a preferred exemplary embodiment, a system user accesses the C3 practitioner and facility tool to populate a facility worksheet to be displayed on his or her remote computer. Once the facility worksheet has been populated, the system user may be able to enter/amend data in fields within the worksheet. In preferred exemplary embodiments, fields of the worksheet have been pre-populated by the C3 Tool upon generation of the worksheet. The process for submitting facility updates and process changes may be the same as those discussed above for submitting practitioner updates and process changes.

In one exemplary embodiment, a system user may enter health care provider data into at least one database of the system. For example, data relating to a health care practitioner, facility, or hospital may not be stored in the database. If that health care practitioner, facility, or hospital is part of a network for which a CMS filing will take place, it may be necessary to add data relating to the practitioner, facility, or hospital to the database so that the system can incorporate it into an HSD table. A system user may be able to send the practitioner, facility, or hospital data directly to the database for storage. In a preferred exemplary embodiment, the system generates a worksheet that the system user completes (the completion resulting in the entry of the practitioner, facility, or hospital data into the worksheet) and is received by one or more servers of the system before the data is added to the database.

Figure 17:
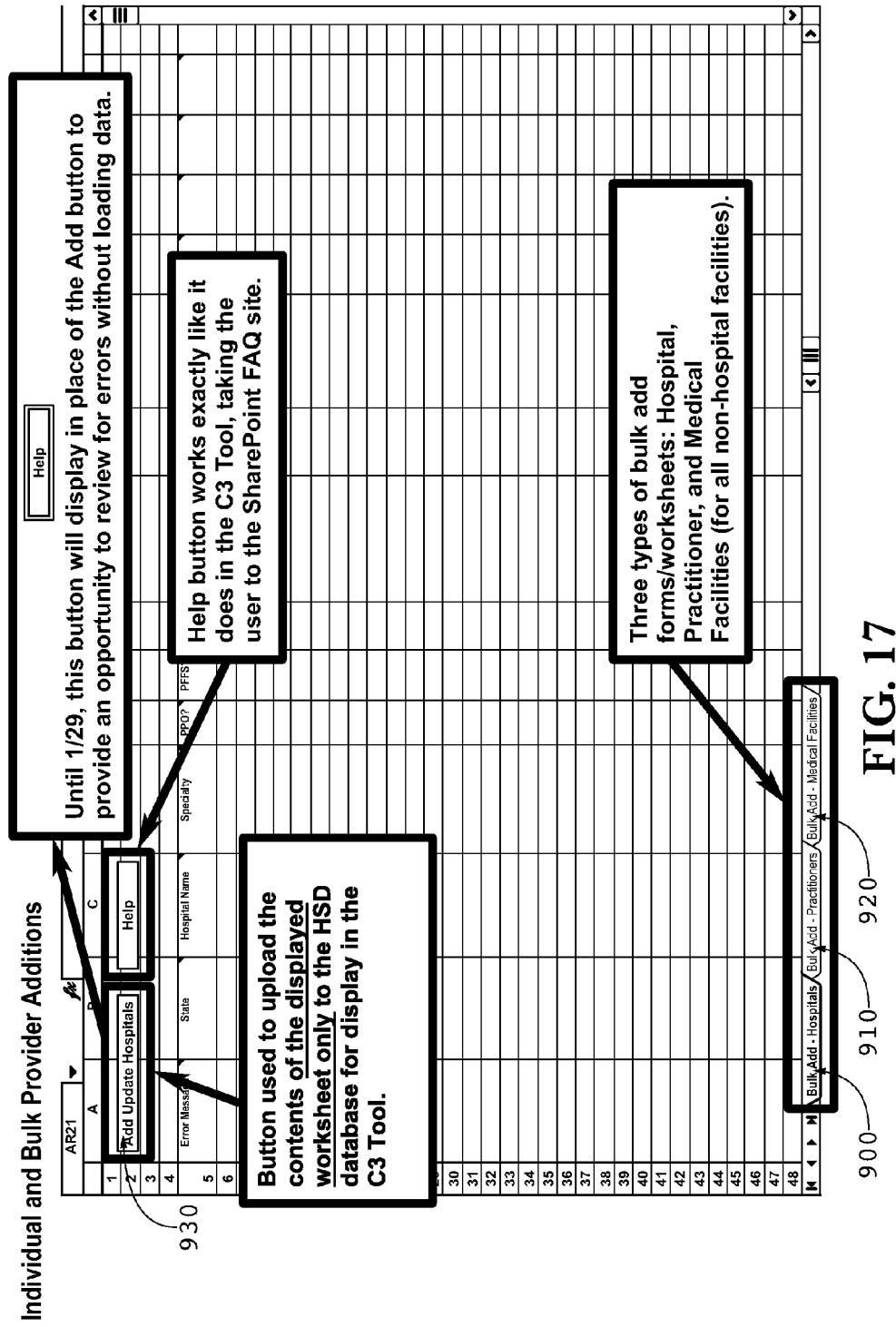
FIG. 17 shows a screenshot of an exemplary embodiment of a worksheet that may be utilized by a system user to add hospital data to the database.

In a preferred exemplary embodiment, one or more servers of the system execute a Bulk Add tool that permits a system user to enter health care provider data for facilities and practitioners into at least one database of the system. In one exemplary embodiment comprising a Bulk Add Tool, the tool sends three worksheets to a remote computer for viewing. FIG. 17 shows an exemplary embodiment of three worksheets that may be sent by a Bulk Add tool for viewing by the remote computer. As shown, the three worksheets in the exemplary embodiment of FIG. 17 consist of a Bulk Add Hospitals worksheet 900, a Bulk Add Practitioners Worksheet 910, and a Bulk Add Facilities worksheet 920. The Bulk Add Facilities worksheet may be utilized to send data for non-hospital health care facilities to the database. A system user may be able to select which of the three worksheets he or she wishes to utilize, enter data into the selected worksheet, and then cause the entered data to be sent to the database as health care service provider data by entering a command into his or her remote computer. In a preferred exemplary embodiment, each worksheet comprises an icon which may be selected by the system user when he or she desires that the data that has been entered into the worksheet be sent to the database. FIG. 17 shows an exemplary embodiment of an icon 930 that may be selected by the user to cause the Bulk Add tool to send the data contained within the worksheet to be sent to the database.

FIG. 18 shows an exemplary embodiment of a worksheet 910 that may be utilized by the Bulk Add Tool to prompt a system user to enter hospital data into the database. As can be seen, the worksheet may comprise an "Add/Update Hospitals" icon 930 as well as a "Help" icon 940. The Add/Update Hospitals icon may be utilized by a system user to cause the hospital data he or she has entered into the worksheet to be sent to the database. The Help icon may be utilized by the system user if he or she is encountering problems using the Bulk Add Tool. As can be seen in the FIG. 18 embodiment, the worksheet may comprise at least one column with a dropdown selector 950 which facilitates the system user's completion of the worksheet. In preferred exemplary embodiments, the dropdown selector is pre-populated with valid entries that may be selected by the system user for incorporation into a given field. For example, there may be predefined hospital specialties that may be assigned to hospitals. A specialty column within the worksheet may comprise a dropdown selector containing a list of the valid hospital specialties. FIG. 18 shows an example of hospital specialties that may be included in a dropdown selector 950 within a specialty column of a worksheet. A worksheet generated by the Bulk Add Tool may include more than one dropdown selector. In a preferred exemplary embodiment a hospital that offers multiple specialties is shown on separate rows of the worksheet—a row for each specialty. In one exemplary embodiment, a Bulk Add worksheet for adding hospital data to the database comprises a field where the hospital's bed count is entered by the system user.

Figure 19:
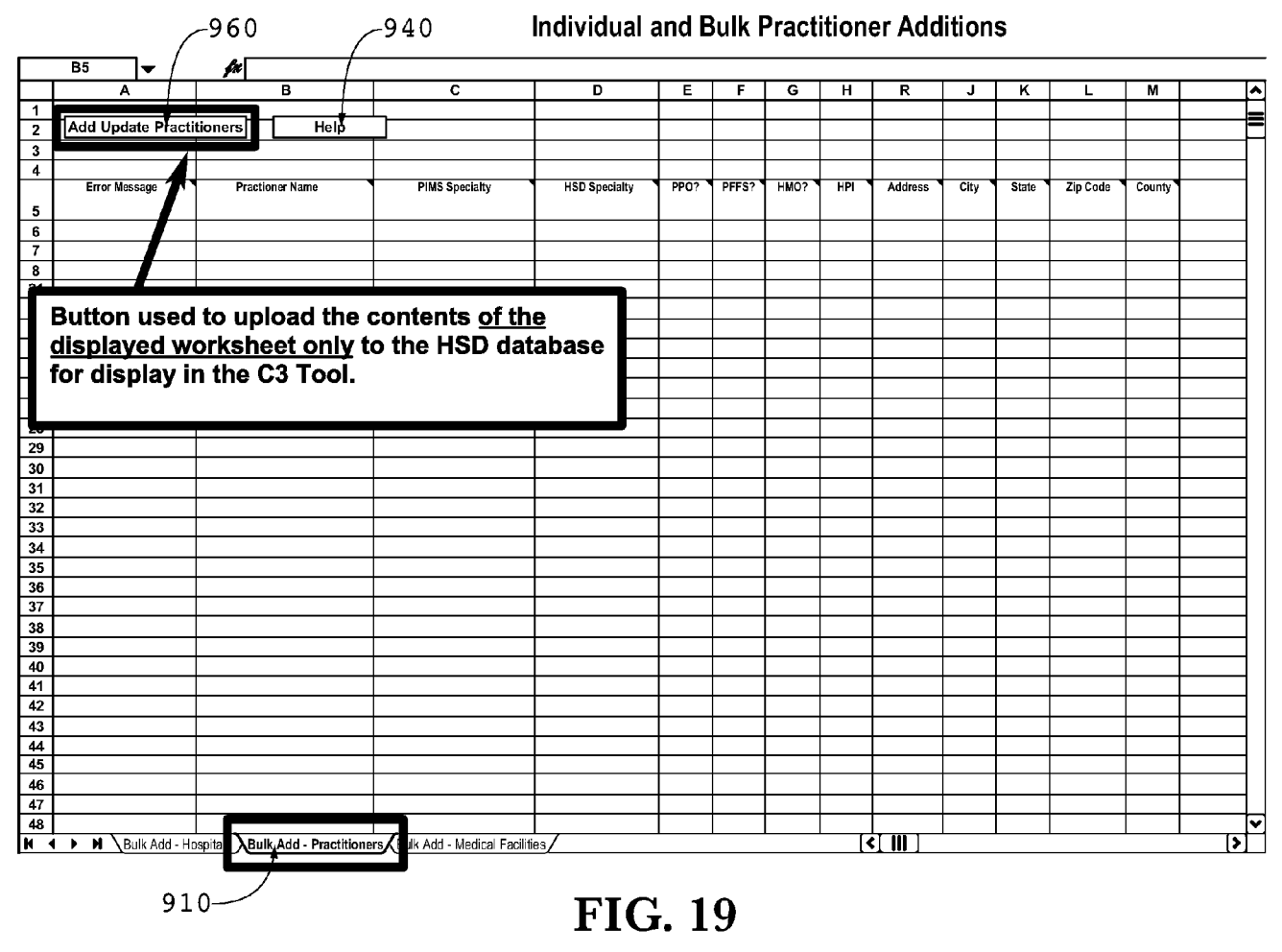
Figure 20:
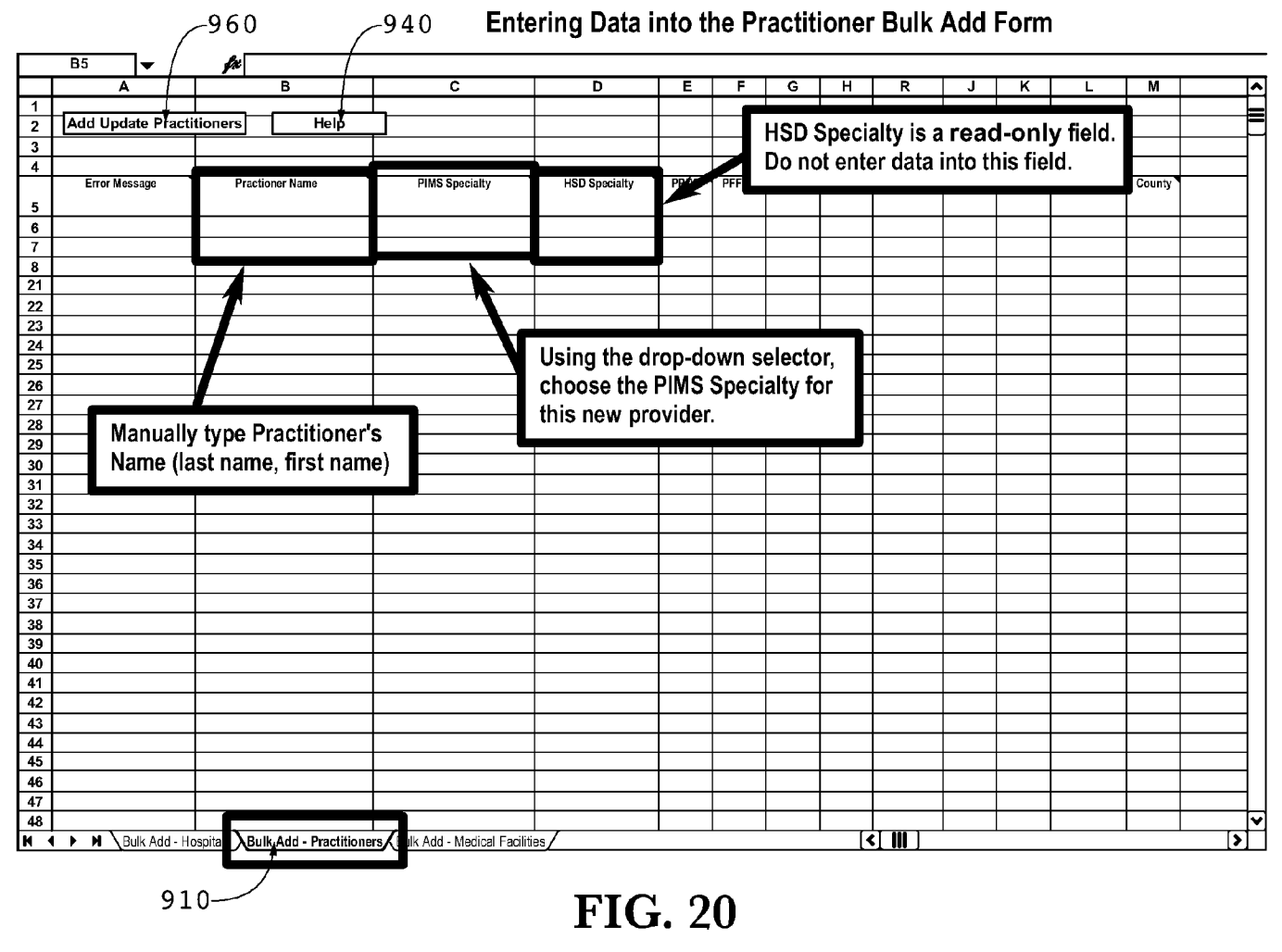

FIG. 19 shows an exemplary embodiment of a worksheet 910 that may be generated by the Bulk Add Tool to prompt a system user to enter practitioner data into the database. As shown, the worksheet may comprise an "Add/Update Practitioners" icon 960 and a "Help" icon 940. The Add/Update Practitioner icon may be selected by a system user when he or she desires that the practitioner data he or she has entered into the worksheet be sent to the database. The Help icon may be selected by a system user if he or she is experiencing technical difficulties utilizing the Bulk Add tool. FIG. 20 shows exemplary columns that may be incorporated into a Bulk Add Practitioner worksheet. As can be seen, some of the columns that may be included comprise: practitioner name; PIMS specialty; HSD specialty; PPO; PFFS; HMO; NPI; Address; City; State; Zip Code; County; and Medical Group Affiliation.

FIG. 21 shows an exemplary embodiment of a worksheet that may be generated by the Bulk Add Tool to prompt a system user to enter medical facility data into the database. As can be seen, the worksheet may comprise an icon for commanding the Bulk Add Tool to send the data that has been entered into the worksheet to the database (in this case an "Add/Update Medical Facilities" icon) and an Icon that may be selected by the system user when he or she needs help using the Bulk Add Tool. FIG. 21 shows exemplary columns that may be included in a Bulk Add Facilities worksheet. As can be seen, the columns that may be included comprise: medical facility name; PIMS specialty; HSD specialty; PPO; PFFS; HMO; Medicare ID; NOI; Address; City; State; Zip Code; County; and Medicare-Certified Bed Count.

In one exemplary embodiment, system users may have reason to utilize the Bulk Add tool to add facility data to the database before they add practitioner data to the database via the Bulk Add Tool. The user may select the Bulk Add tool if a practitioner worksheet requires the entry of a corresponding facility for a practitioner and the facility where the practitioner works has not yet been entered in the system. For example, a practitioner worksheet may utilize a dropdown selector within a facility column where the dropdown selector contains a list of the facilities that have been entered into the database. If the facility where the practitioner works has not yet been entered into the database, it is not available for selection in this example. Thus, to enter the correct facility for the practitioner, the system user first needs to utilize the Bulk Add tool to add the facility to the database prior to adding the practitioner.

In one exemplary embodiment, the Bulk Add tool may not send data to the database when the data entered by a system user into a Bulk Add Worksheet contains at least one error. When a system user requests that the data entered into a Bulk Add worksheet be sent to the database, the Bulk Add tool may process the data within the worksheet to see if the data contains errors. If the data contains errors, the Bulk Add Tool may send a message to the remote computer of the system user that the data he or she has entered into the Bulk Add worksheet contains at least one error. In a preferred exemplary embodiment, the Bulk Add Tool indicates within the Bulk Add worksheet which data entry contained an error. The system user may correct the error and then request that the data within the worksheet be sent to the database. In some exemplary embodiments, the system user sends some of the data contained within the worksheet to the database (those entries that did not contain errors) and the database is updated with the data for which errors existed when the system user initially attempted to send all the entries to the database. In other words, provider data that already exists in the database is not loaded again.

In a preferred exemplary embodiment, once a system user has added practitioner or facility data into the database via the Bulk Add Tool, the C3 Practitioner and Facility Tool may be able to retrieve the data from the database upon receiving search parameters from a remote computer. Once the data has been retrieved from the database, the C3 Tool may incorporate the data into practitioner or facility tables that are sent to the remote computer for viewing. This feature may permit system users to utilize the C3 Tool to cause amendments to be made to the practitioner and facility data as has been discussed.

In some exemplary embodiments, the system generates final files that may be reviewed by system users. In a preferred exemplary embodiment, a final file contains health care service provider data from the database that has been assembled into an HSD table. The HSD table is preferably in a form compatible for filing with CMS to obtain approval of a Medicare plan. In some embodiments, once the system has generated a final file, it is sent to a remote computer for display. The final file preferably displays notification of any errors that may be contained in the data. A system user may be able to review the final file, utilize the file's error notifications to correct errors within the data, and approve the final file for filing with CMS.

Figure 22:
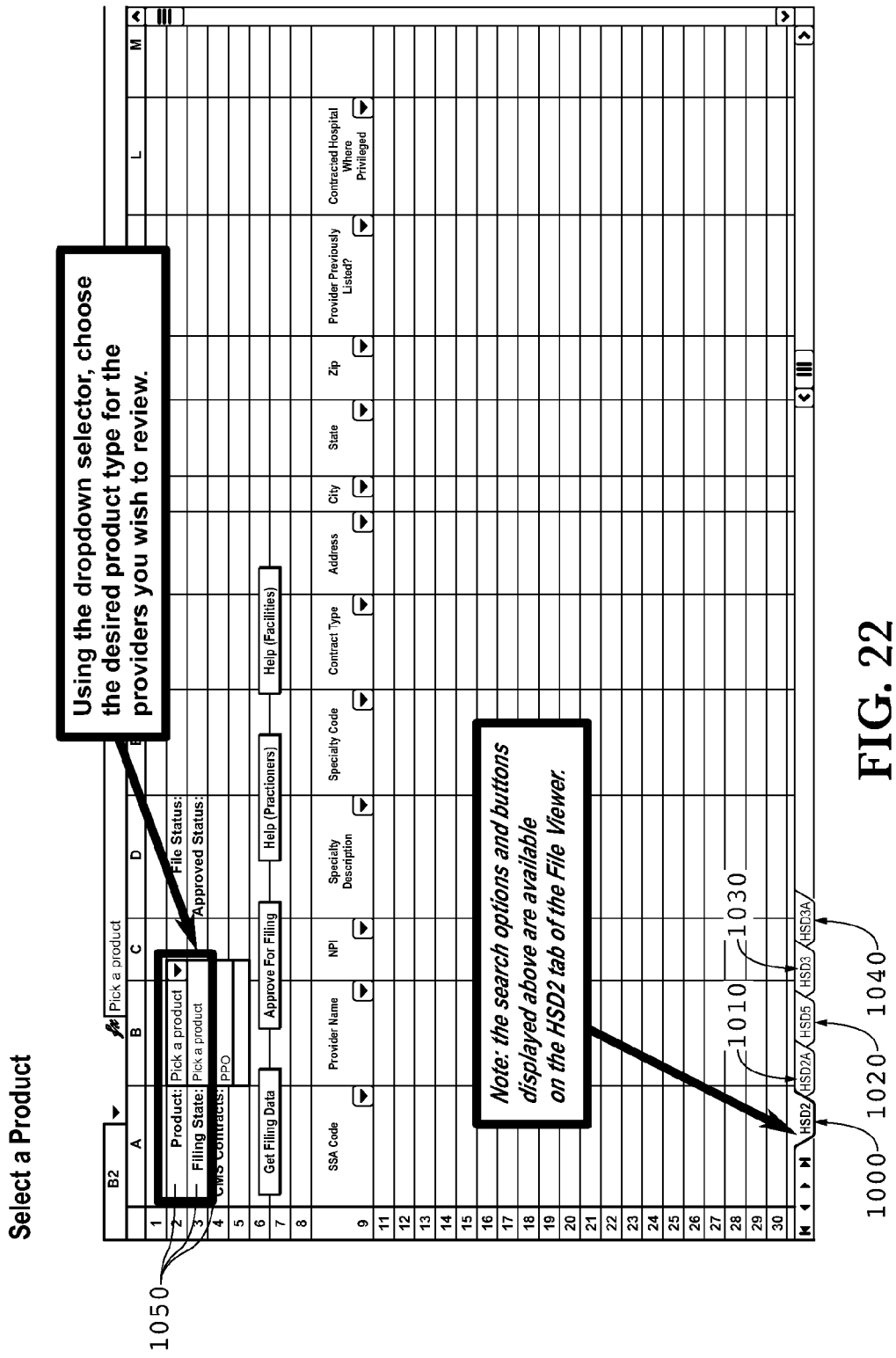
FIG. 22 shows a screenshot of an exemplary embodiment of a worksheet that may be utilized by the system to display final files.
Figure 23:
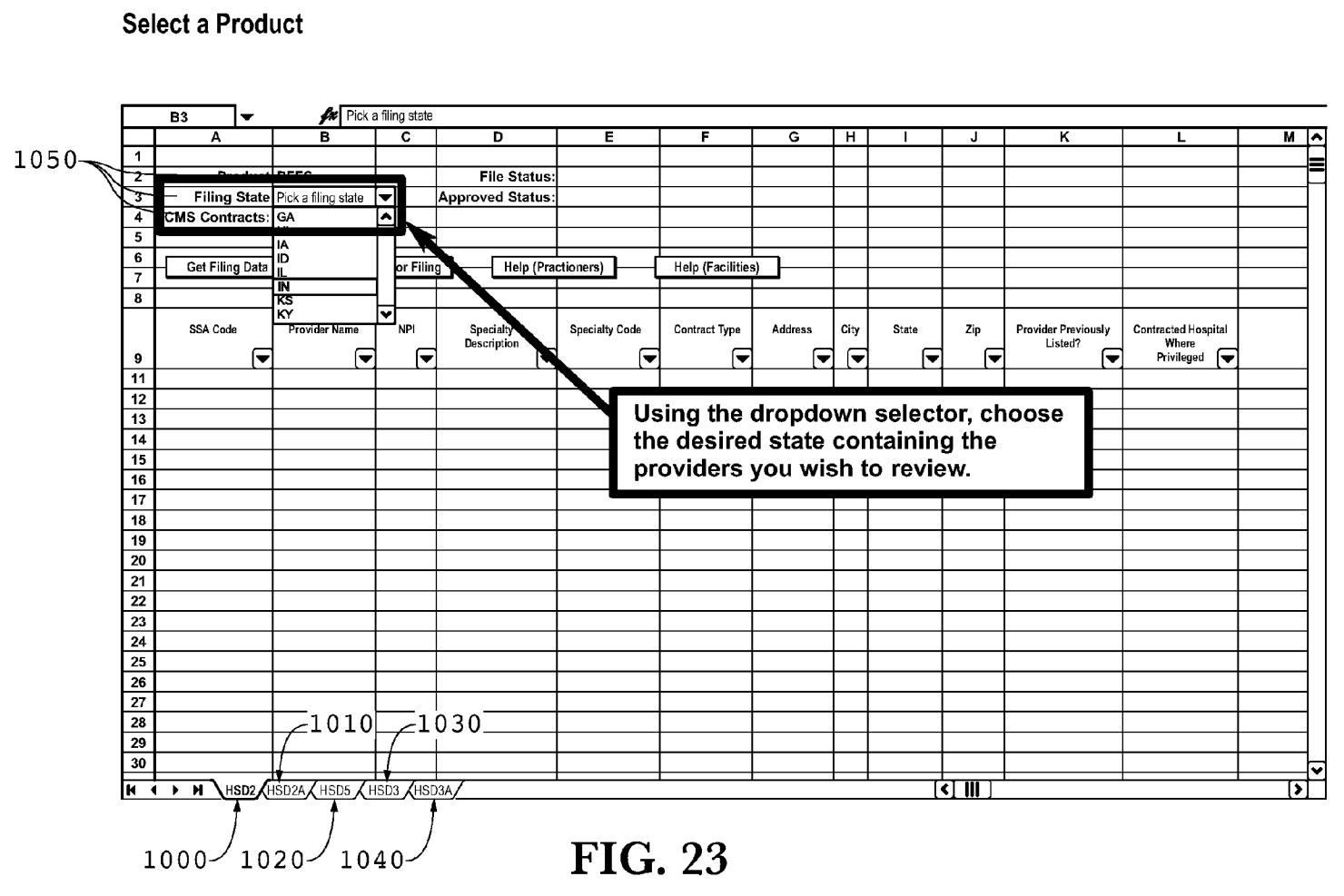
Figure 24:
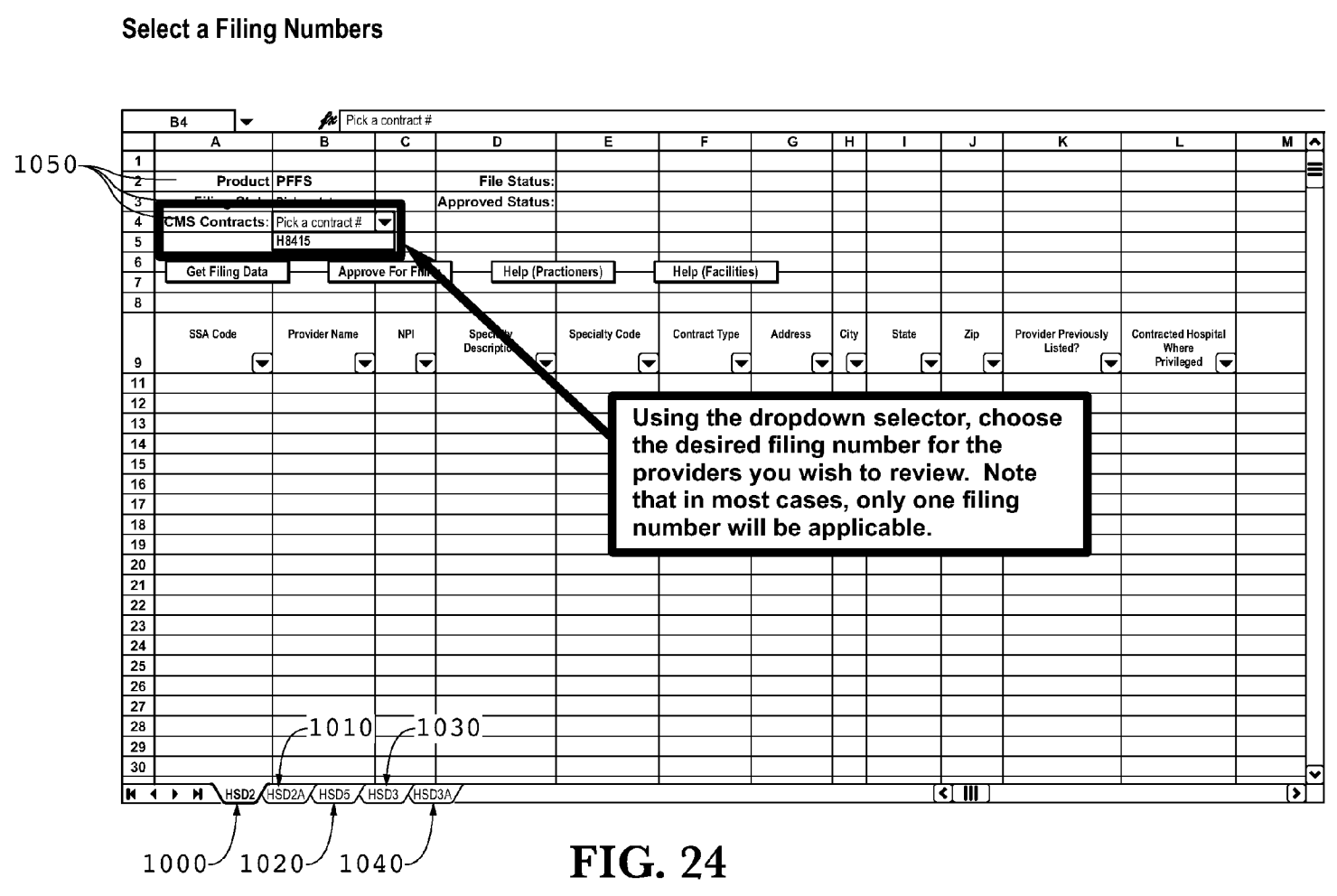
Figure 25:
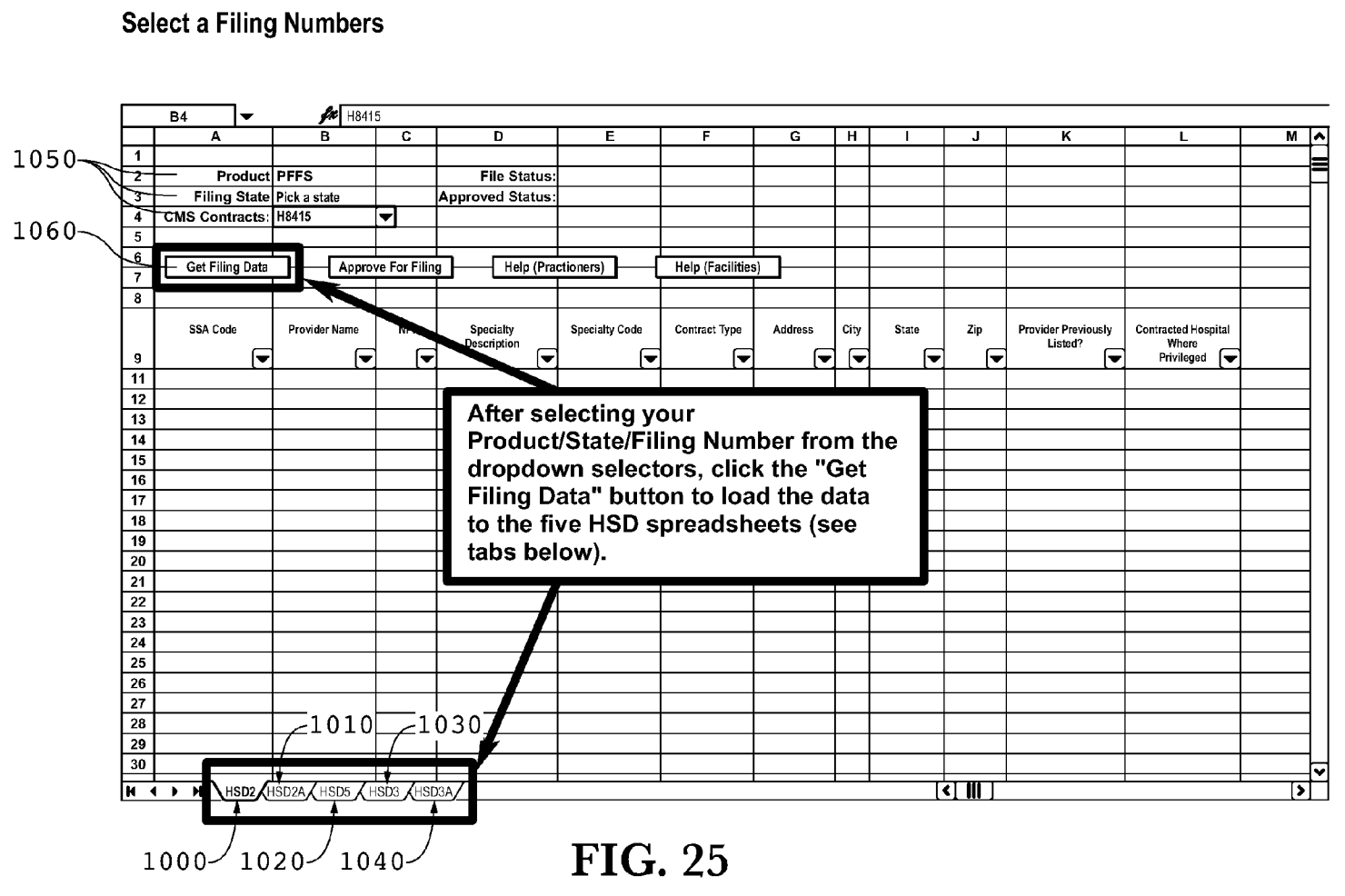

In one exemplary embodiment, one or more servers of the system execute a Final File Viewer tool. In a preferred exemplary embodiment the Final File Viewer Tool is utilized through a Microsoft Excel document. An exemplary embodiment of an Excel document being utilized to run a Final File Viewer is shown in FIG. 22. As shown, some exemplary Excel documents may contain five worksheets: an HSD2 worksheet 1000; and HSD2A worksheet 1010; an HSD5 worksheet 1020; an HSD3 worksheet 1030; and an HSD3A worksheet 1040. In a preferred exemplary embodiment as shown in FIG. 22, at least one worksheet comprises search parameters 1050 that may be completed by a system user. In the exemplary embodiment shown, the search parameters comprise product, filing state, and CMS contract number. A system user may use dropdown selectors to choose an entry for each of the search parameter fields. FIG. 23 shows an exemplary embodiment of a dropdown selector being utilized to select a filing state search parameter while FIG. 24 shows an exemplary embodiment of a dropdown selector being utilized to enter a CMS Contract # search parameter. Once a selection has been made in each search parameter field, a system user may be able to enter a command for the Final File Viewer tool to retrieve data from the database in order to populate at least one worksheet within the Excel document. In an exemplary embodiment, such as that shown in FIG. 25, a system user may enter a command to retrieve data by selecting a "Get Filing Data" icon 1060 displayed on at least one of the worksheets. In a preferred exemplary embodiment, once a command to retrieve data has been entered by a system user, the Final File Viewer tool retrieves data from the database in accordance with the received search parameters and causes all of the worksheets within the Excel document to be populated with the appropriate data. In a preferred exemplary embodiment, the data is populated into the worksheets in the same format in which it will be filed with the CMS for the approval of a Medicare Advantage plan.

Figure 26:
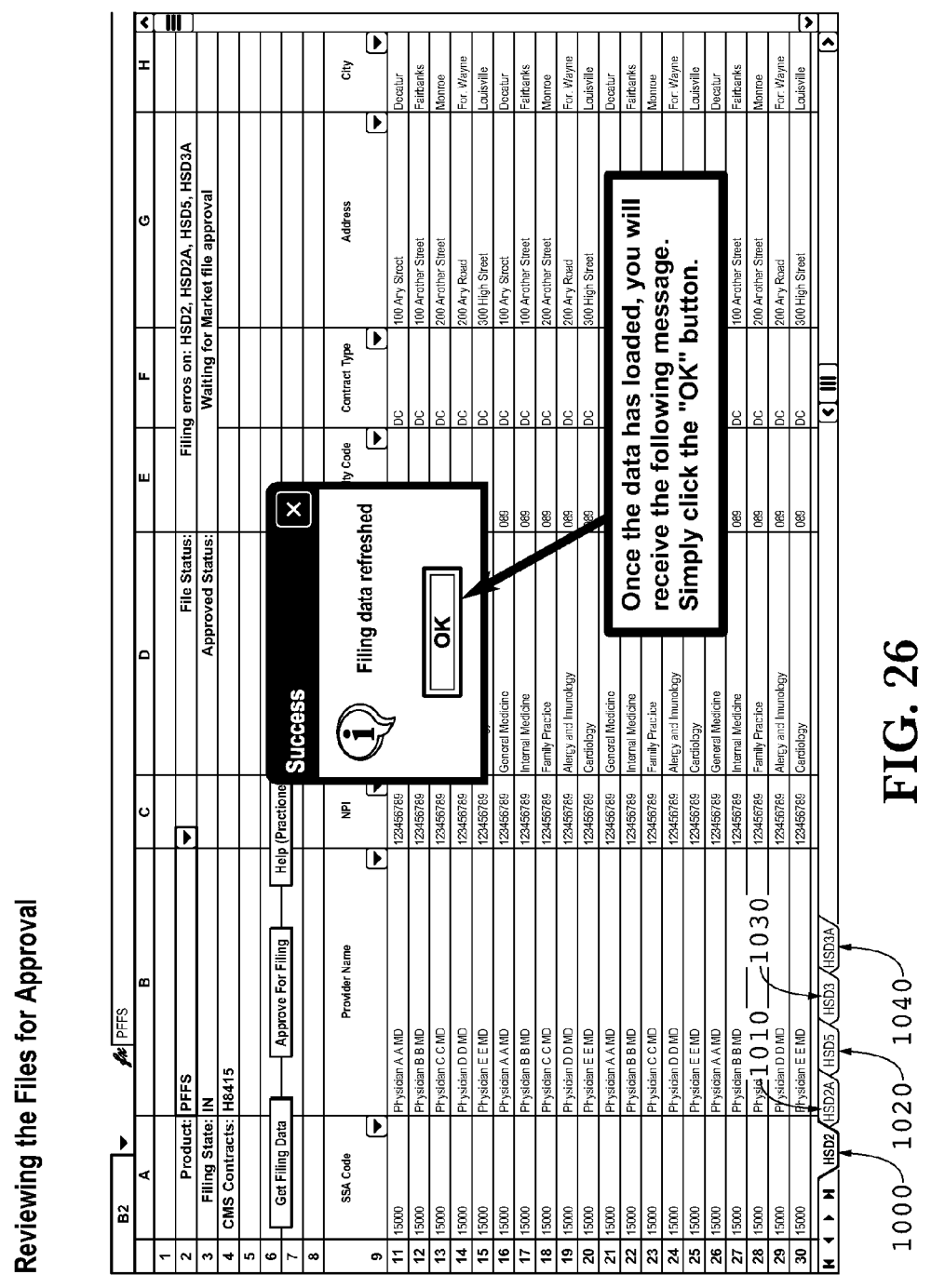
Figure 27:
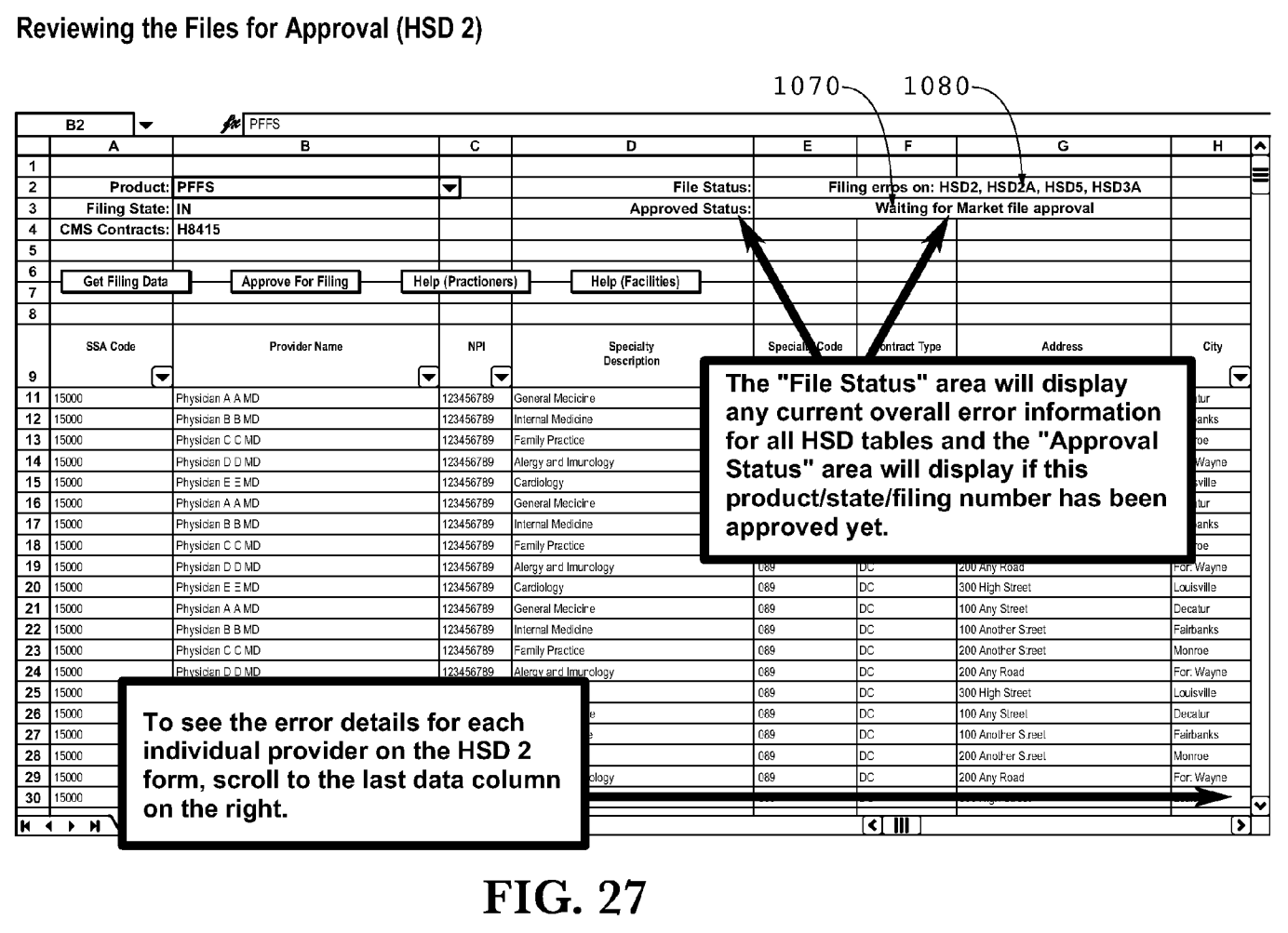
Figure 28:
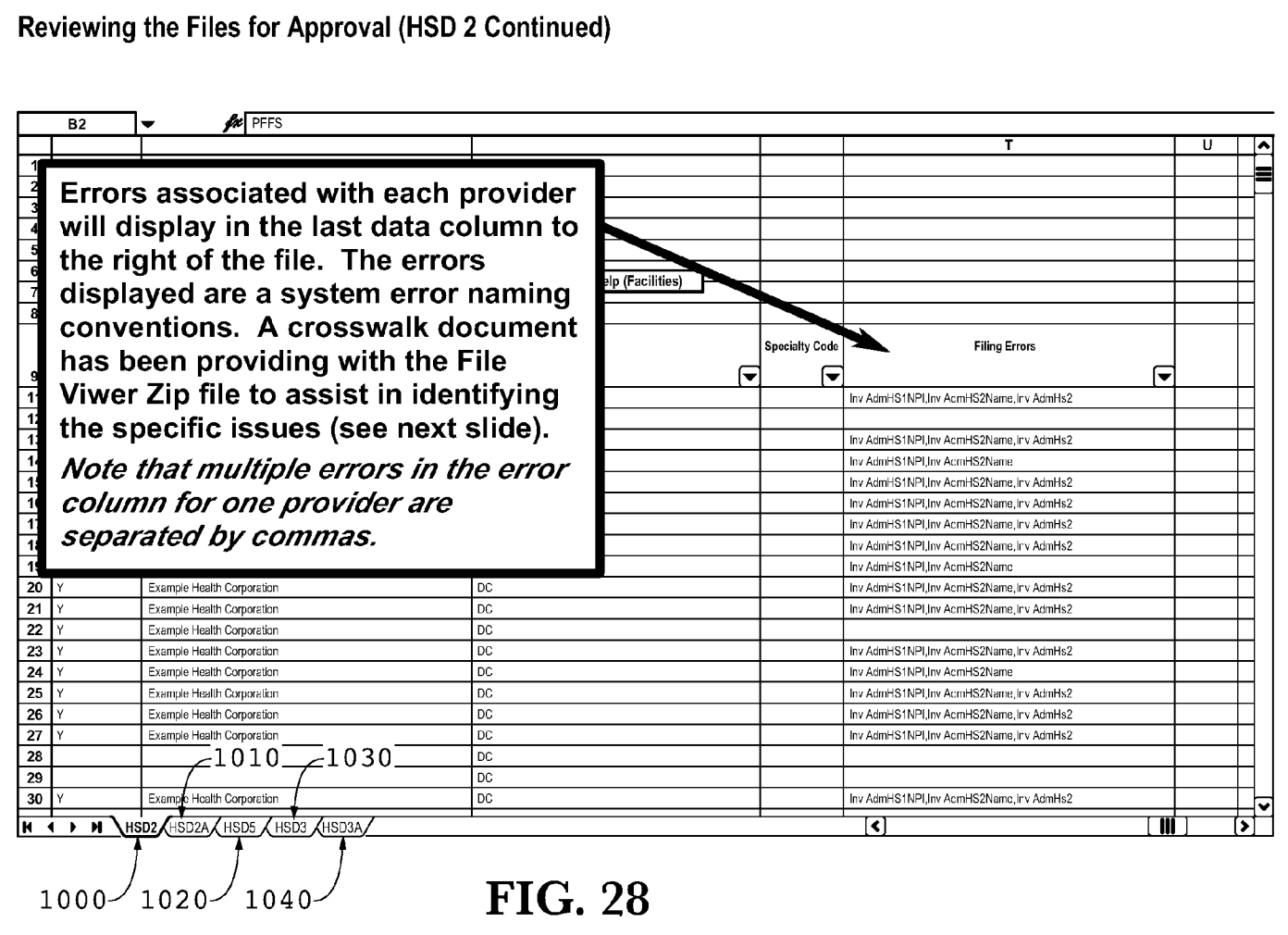
Figure 29:
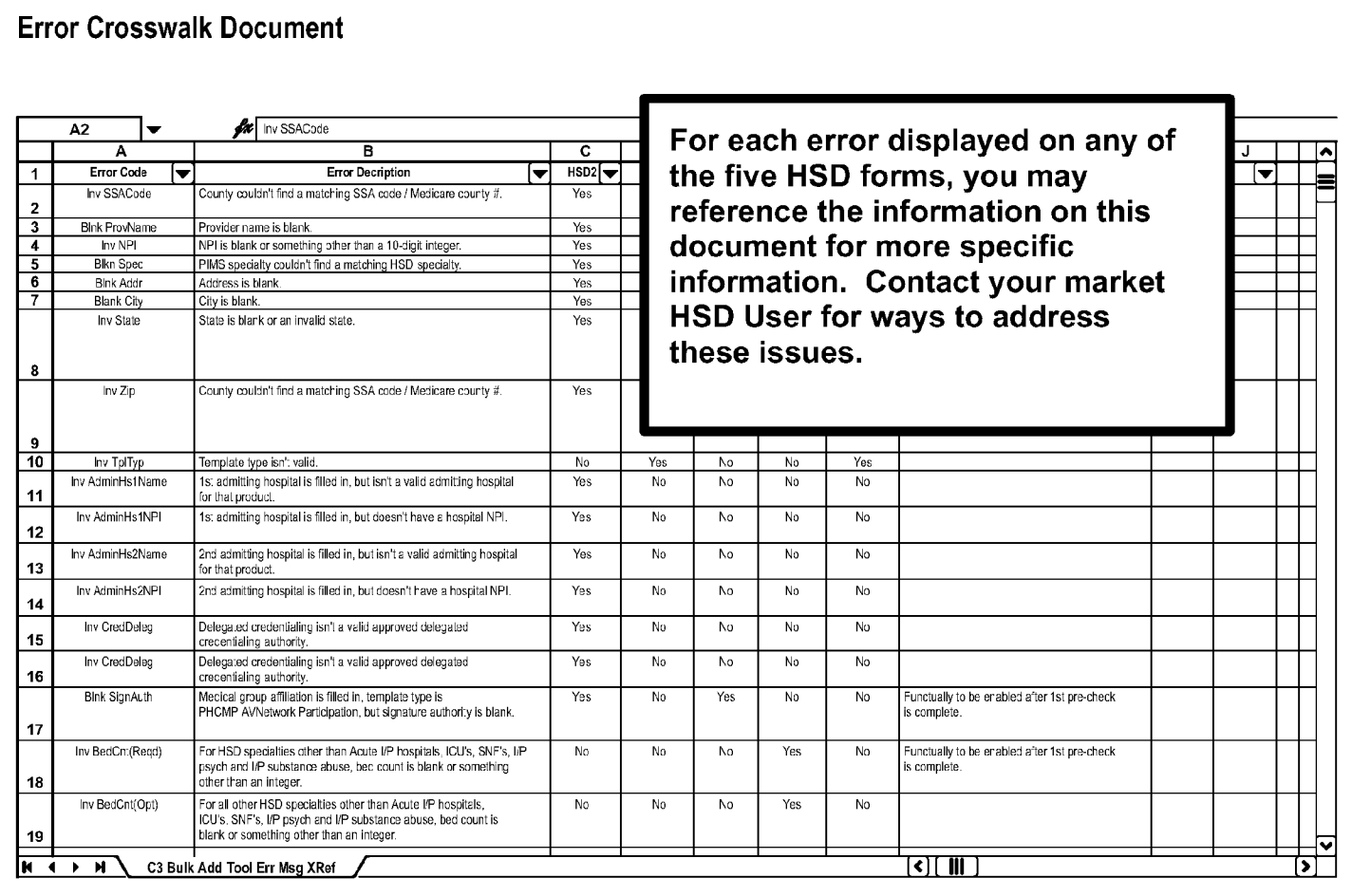

In an exemplary embodiment, once the Final File Viewer Tool has been populated with health care provider data as shown in FIG. 26, the computerized system reviews the data. As shown in FIG. 26, the system may send a message to the system user when the data has correctly loaded into the worksheet(s). As shown in FIG. 27, a worksheet may display a "File Status" area 1070 which lists any worksheet(s) currently containing an error. An error may be an incorrect data entry or an empty field that could cause the final HSD table and corresponding application to be rejected by CMS. The exemplary embodiment shown in FIG. 27 additionally comprises an "Approval Status" area 1080 which indicates whether or not the data contained in the worksheet has been approved for filing with CMS. In some exemplary embodiments, Final File worksheets may provide error details for data entries containing errors. FIG. 28 shows an exemplary embodiment of how a Final File worksheet may provide error details. If those error details are provided in shorthand or code, the system may provide system users with a reference document that facilitates the interpretation of the shorthand and code. An exemplary embodiment of a document that may be provided by the system to assist in the translation of error codes is shown in FIG. 29.

Figure 31:
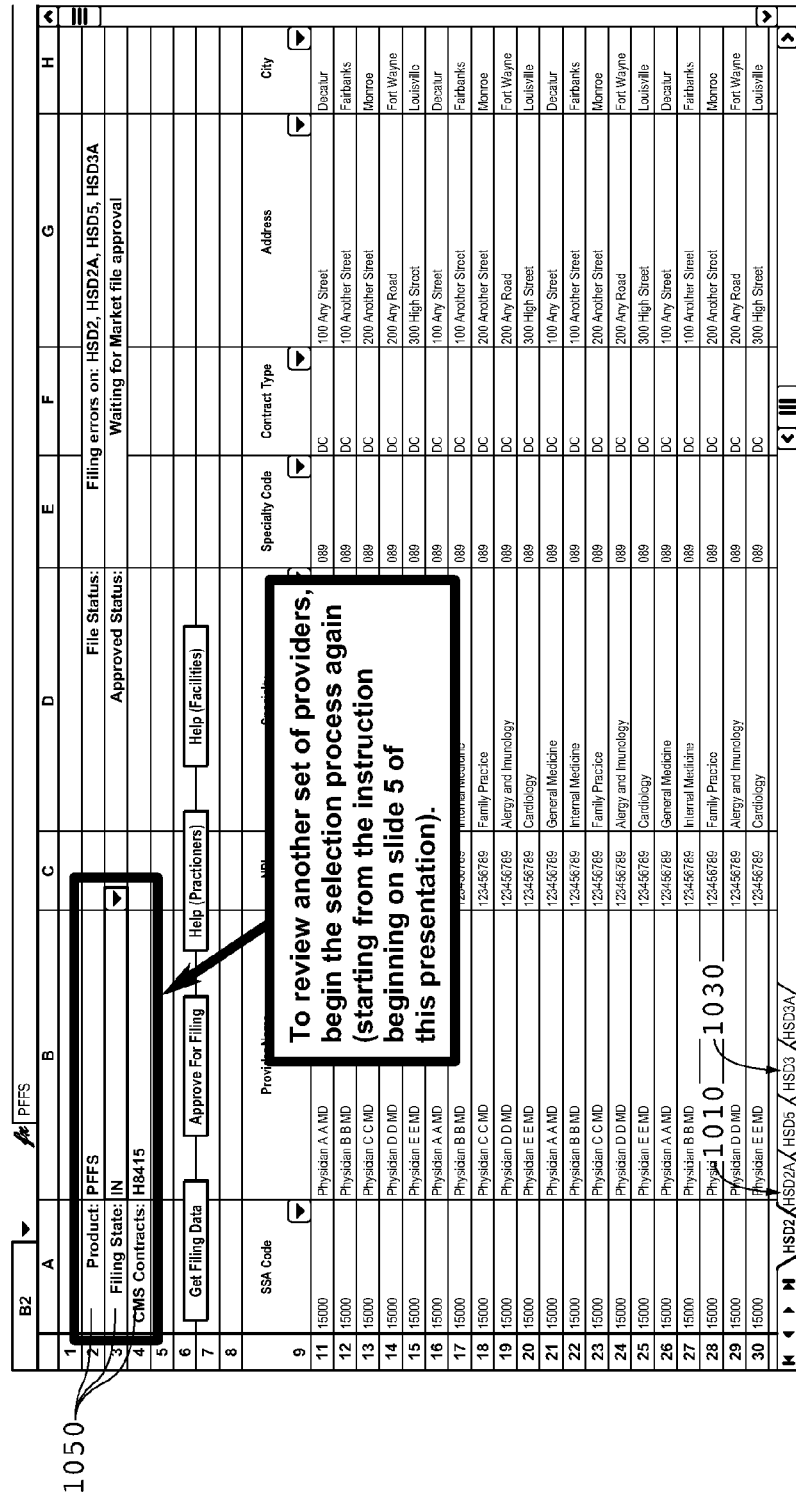
FIG. 31 shows a screenshot of an exemplary embodiment of different search parameters that may be selected by a system user to instruct the system to generate new final files.

In one exemplary embodiment, a system user may utilize a Final File Viewer Tool to approve a table displayed on his or her remote computer for filing with CMS. In a preferred exemplary embodiment, such as that shown in FIG. 30, a system user may not approve a displayed table for filing with CMS until all errors within the table have been corrected. Other tools of the system may need to be utilized to correct errors within the displayed table. For example, a system user may need to access the C3 Practitioner and Facility Tool to pull up the provider data for which errors exist and request amendments be made to the data utilizing update request form templates. Once all errors within a Final File table have been corrected, a system user may be able to enter a command that the data within the table be approved for filing with CMS. A system user may be able to review a new set of tables within the Excel document by entering new search parameters into the displayed fields as shown in FIG. 31 and entering a command that the Final File Viewer Tool retrieve data in accordance with the entered parameters.

In some exemplary embodiments, the system is able to analyze data contained within a final file that has been generated by the system to determine whether the network represented by the data passes requirements that have been set by CMS. In cases where the analysis shows that the network is unlikely to pass CMS requirements, the system may analyze the data within the database to add qualified health care providers to the network until the network passes CMS requirements. In a preferred exemplary embodiment, the system utilizes the number of health care providers within a network, as well as the location of the health care providers to assess the adequacy of the network.

In some exemplary embodiments, one of more servers of the system runs a Network Adequacy Tool that analyzes data within a final file to determine whether the network represented within the file is adequate. The tool is preferably an automated tool that analyzes data within Final File tables of the system to determine whether or not minimum Medicare requirements are being met. Medicare maintains requirements to be met before a private company may offer a Medicare Advantage plan. The minimum criteria currently vary by specialty type (e.g., cardiology, ophthalmology, etc.) and the geography of the region. Criteria includes a minimum number of providers/beds, and maximum travel distances and times. Based on Medicare requirements, a minimum number of providers must be included within the network. Providers' inclusion in a plan is not restricted by their physical location within a given county as Medicare also permits providers to be included in a network if they serve beneficiaries within the county in question and meet Medicare's maximum time and distance requirements. These providers are referred to as "supplemental providers" for the plan in question. Similarly, Medicare allows consideration of local established patterns of care and other factors that govern reasonable access which permits additional providers to be included in a network in some instances. These providers are referred to as "pattern of care" providers.

In one exemplary embodiment, the network adequacy tool analyzes the data contained within a Final File of the system and determines whether or not the requirements of CMS would be met by the network of providers included in the table. For example, CMS has established network access parameters for most provider types/specialties included on HSD tables. Those parameters specify the maximum distance (in miles) a member should travel to one or more provider service locations. CMS has additionally established "minimum provider" counts required to meet network adequacy standards within each county. The network adequacy tool may analyze the provider data within the final file tool to determine whether the network access parameters and minimum provider counts established by CMS have been satisfied. In cases where analysis shows the network access parameters and minimum provider counts established by CMS have not been satisfied, the network adequacy tool may search through the provider data within the database to find providers that satisfy the network's "supplemental provider" criteria (by utilizing county coverage data for example) to tag providers for the network in question until the access parameters and minimum provider counts have been satisfied.

FIGS. 32, 33, 34, and 35 show exemplary embodiments of tables that may be produced by a Network Adequacy tool to indicate to a system user which networks are adequate according to CMS standards and which are not. FIG. 32 shows an exemplary summary report table that may be generated by the system that permits system users to determine contracting success for specialties where CMS has mandated an access standard. In preferred exemplary embodiments, the table allows users to filter to a specific product and/or a Network VP who owns contracting resources within a specific geography. Upon receiving the filter information entered by the system user, the system may then populate the table with the total number of counties under the specified filter, the number of counties that will pass access standards, the number of counties (Gap) that are not currently passing the access standards, the number of counties where access standards cannot be met due to a lack of providers who meet CMS standards, and counties where additional contracting work is needed (Net Gap). FIG. 33 shows an exemplary summary level report table that may be generated by the system that allows system users to determine contracting success by county for specialties where CMS has mandated an access standard. The system may populate the table with the total number of specialties by product, Network VP, state and county. The specialties may then be broken into the same classifications as shown in the exemplary table of FIG. 32 with the addition of grouping bands. In a preferred exemplary embodiment the table will comprise an ExBand, a GapBand, and TotBand where the ExBand shows the number of specialties where adequacy cannot be met based on the available providers, GapBand shows the number of specialties where additional contracting work is needed, and TotBand shows the total number of specialties that are not passing the CMS access requirements.

FIG. 34 shows an exemplary embodiment of a table that may be generated by the system that allows users to filter to a specific product or state. Once the filters have been selected and received by the system, the system may populate the table with the passing status for every specialty with CMS access requirements by Network VP, state, and county. Cells within the table may be color-coded to provide an easy review of the status of each specialty. FIG. 35 shows an exemplary embodiment of a table that may be generated by the system that allows users to filter to specific product, state, county, and specialty combinations to return data for aid in contracting efforts. The data returned by the system preferably includes providers showing as uncontracted and available based on information contained in the system's database along with their address information, average distance to Medicare beneficiaries, and overall importance. By contracting high importance providers, it may be possible to build a strong network of Medicare providers for submission to CMS via the HSD process. As shown in the exemplary embodiment of FIG. 35, the FoundIn column displays from where the provider information has been obtained. The source values may comprise AMA (American Medical Association), Comp (Competitor website), Suppl (contracted, but not physically located within the county), and Incnty (contracted and physically located within the county). The report may also display the percentage of Medicare beneficiaries for whom access can be met. Values that may be generated by the system include access met by providers physically in county; in county and supplemental to the county; and in county, supplemental, and available per AMA.

Having shown and described exemplary embodiments of the present invention, those skilled in the art will realize that many variations and modifications may be made to the described invention and still be within the scope of the claimed invention. Thus many of the elements indicated above may be altered or replaced by different elements which will provide the same or substantially the same result and fall within the spirit of the claimed invention. It is the intention, therefore, to limit the invention only as indicated by the scope of the following claims:

The invention claimed is:

1. A computerized method for generating a health services delivery table comprising:
  a database storing health care provider data and one or more servers executing programming instructions to:
  (a) receive at least one search parameter from a remote computer;
  (b) retrieve health care provider data from the database in compliance with the at least one search parameter;
  (c) transmit the health care provider data to the remote computer for viewing;
  (d) receive a first request from the remote computer to generate a final file that comprises:
    (1) a health services delivery table comprising the health care provider data; and
    (2) a message for each error contained within the health care provider data of the health services delivery table;
  (e) transmit the final file to the remote computer for viewing;
  (f) in response to at least one error message, receive from the remote computer amended health care provider data;

(g) update the database with the amended health care provider data;
(h) receive a second request from the remote computer to approve the final file for filing; and
(i) transmit to the remote computer confirmation that the final file contains no errors.

2. The method of claim 1 further comprising programming instructions to:
(j) receive from the remote computer a request to confirm the adequacy of a network according to:
(1) number of health care providers in the network; and
(2) location of health care providers in the network; and
(k) transmit to the remote computer an indication of adequacy of the network.

3. The method of claim 2 further comprising programming instructions to:
(l) search the health care provider database to identify additional health care providers to add to the network; and
(m) transmit to the remote computer identification data for additional health care providers to increase adequacy of the network.

4. The method of claim 1 further comprising programming instructions to:
(j) receive a command to file the approved final file with a health care services agency; and
(k) electronically transmit the approved file to the health care services agency.

5. The method of claim 1 wherein the health care provider data is electronically transmitted to the remote computer for viewing in the form of a worksheet.

6. The method of claim 1 further comprising programming instructions to:
(j) receive a request from the remote computer to view a document that translates the list of errors displayed by the final file; and
(k) transmit the document to the remote computer for viewing.

7. The method of claim 1 further comprising programming instructions to:
(j) receive a request from the remote computer to add health care provider data to the database; and
(k) update the database with the additional health care provider data.

8. A computerized method for generating a health services delivery table comprising:
a database storing health care provider data and one or more servers executing programming instructions to:
(a) receive at least one health care practitioner search parameter from a remote computer;
(b) retrieve health care practitioner data from the database in compliance with the at least one search parameter where the retrieved health care practitioner data comprises:
(i) practitioner contact data;
(ii) practitioner term data; and
(iii) practitioner owner data;
for at least one health care practitioner;
(c) populate a worksheet displayed by the remote computer with the health care practitioner data retrieved from the database;
(d) receive a request to view at least one practitioner update request form selected from the group consisting of practitioner contact update request form, practitioner term update request form, and practitioner owner update request form;
(e) send the requested at least one practitioner update request form to the remote computer for viewing and completion by a user;
(f) receive a request to amend the health care practitioner data in the database in accordance with the at least one update request form;
(g) update the database with the amended health care practitioner data;
(h) receive a first request from the remote computer to generate a final file comprising:
(1) a health services delivery table comprising the health care practitioner data; and
(2) a message for each error contained within the health care practitioner data of the health services delivery table; and
(i) receive a second request from the remote computer to approve the final file for filing when no errors are identified within the health care practitioner data of the final file.

9. The method of claim 8 further comprising programming instructions to:
(j) receive from the remote computer a request to confirm the adequacy of a network according to:
(1) number of health care practitioners in the network; and
(2) location of health care practitioners in the network;
(k) transmit to the remote computer an indication of adequacy of the network.

10. The method of claim 9 further comprising programming instructions to:
(l) search the health care provider database to identify additional health care practitioners to add to the network; and
(m) transmit to the remote computer identification data for additional health care practitioners to increase adequacy of the network.

11. The method of claim 8 further comprising programming instructions to:
(j) receive a command to file the approved final file with a health care services agency; and
(k) electronically transmit the approved final file to the health care services agency.

12. The method of claim 8 further comprising programming instructions to:
(j) receive at least one health care facility search parameter from the remote computer;
(k) retrieve health care facility data from the database in compliance with the at least one health care facility search parameter wherein the retrieved health care facility data comprises:
(i) facility contact data;
(ii) facility term data; and
(iii) facility owner data;
for at least one health care facility;
(l) populate a worksheet displayed by the remote computer with the health care facility data retrieved from the database;
(m) receive a request to view at least one facility update request form selected from the group consisting of facility contact update request form, facility term update request form, and facility owner update request form;
(n) send the requested at least one facility update request form to the remote computer for viewing and completion by a user;
(o) receive a request to amend the health care facility data in the database in accordance with the at least one update request form;

(p) receive a third request from the remote computer to generate a final file that comprises:
  (1) an health services delivery table comprising the health care facility data; and
  (2) a message for each error contained within the health care facility data of the health services delivery table; and
(q) receive from the remote computer a fourth request to approve the final file for filing when no errors are identified within the health care facility data of the final file.

13. The method of claim 12 further comprising programming instructions to:
  (r) receive a command to electronically file approved final files with a health care services agency; and
  (s) electronically transmit approved files to the health care services agency.

14. The method of claim 12 further comprising programming instructions to:
  (r) receive a command to view a document that translates all errors contained in the final file documents; and
  (s) transmit the document to the remote computer for viewing.

15. A computerized method for generating a health services delivery table comprising:
  a database storing health care provider data and one or more servers wherein the one or more servers execute programming instructions to:
  (a) receive from a remote computer a request to amend the health care provider data stored in the database;
  (b) update the database with the amended healthcare provider data;
  (c) receive a request to generate a final file that comprises a health services delivery table, the request comprising:
    (1) a filing state; and
    (2) a contract number for a health care services agency;
  (d) generate a final file in accordance with the received request and search parameters;
  (e) transmit the final file to the remote computer for viewing; and
  (f) receive an indication from the remote computer that the final file is approved for filing.

16. A computerized system for generating a health services delivery table comprising:
  at least one database storing health care provider data; and
  one or more servers connected to a public network where the one or more servers are configured to:
  (a) receive from a remote computer a request to amend the health care provider data stored in the database;
  (b) update the database with the amended health care provider data;
  (c) receive a request to generate a final file that comprises a health services delivery table, the request comprising:
    (1) a filing state; and
    (2) a contract number for a health care services agency;
  (d) generate a final file in accordance with the received request and search parameters;
  (e) transmit the final file to the remote computer for viewing; and
  (f) receive an indication from the remote computer that the final file is approved for filing.

17. The system of claim 16 wherein the one or more servers is further adapted to:
  (g) generate a list of errors contained in the final file.

18. The system of claim 17 wherein the one or more servers is further adapted to:
  (h) receive a request to electronically transmit the approved final file to a health care services agency.

19. The system of claim 16 wherein the one or more servers is further adapted to:
  (g) receive from the remote computer a request to confirm the adequacy of a network according to:
    (1) number of health care providers in the network; and
    (2) location of health care providers in the network; and
  (h) transmit to the remote computer an indication of adequacy of the network.

20. The system of claim 19 wherein the one or more servers is further adapted to:
  (i) search the health care provider database to identify additional health care providers to add to the network; and
  (j) transmit to the remote computer identification data for additional health care providers to increase adequacy of the network.

* * * * *